United States Patent
Suzuki et al.

(10) Patent No.: US 12,421,412 B2
(45) Date of Patent: Sep. 23, 2025

(54) TEXTILE PRINTING PRETREATMENT LIQUID, TEXTILE PRINTING INK SET, INK JET TEXTILE PRINTING METHOD, PRINTED TEXTILE, AND ONIUM SALT COMPOUND

(71) Applicant: FUJIFILM CORPORATION, Tokyo (JP)

(72) Inventors: Shota Suzuki, Kanagawa (JP); Shinichiro Sekine, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 510 days.

(21) Appl. No.: 17/702,808

(22) Filed: Mar. 24, 2022

(65) Prior Publication Data

US 2022/0213343 A1 Jul. 7, 2022

Related U.S. Application Data

(63) Continuation of application No. PCT/JP2020/031883, filed on Aug. 24, 2020.

(30) Foreign Application Priority Data

Sep. 30, 2019 (JP) ................. 2019-180625

(51) Int. Cl.
| | |
|---|---|
| C09D 11/54 | (2014.01) |
| B41J 2/01 | (2006.01) |
| B41J 3/407 | (2006.01) |
| B41M 5/00 | (2006.01) |
| C07C 211/62 | (2006.01) |
| C09D 11/033 | (2014.01) |
| C09D 11/037 | (2014.01) |
| C09D 11/10 | (2014.01) |
| C09D 11/102 | (2014.01) |
| C09D 11/328 | (2014.01) |
| C09D 11/38 | (2014.01) |

(Continued)

(52) U.S. Cl.
CPC .............. C09D 11/54 (2013.01); B41J 2/01 (2013.01); B41J 3/4078 (2013.01); C07C 211/62 (2013.01); C09D 11/033 (2013.01); C09D 11/037 (2013.01); C09D 11/10 (2013.01); C09D 11/102 (2013.01); C09D 11/328 (2013.01); C09D 11/38 (2013.01); C09D 11/40 (2013.01); D06P 1/5285 (2013.01); D06P 1/66 (2013.01); D06P 5/002 (2013.01); D06P 5/30 (2013.01); B41M 5/00 (2013.01)

(58) Field of Classification Search
None
See application file for complete search history.

(56) References Cited

U.S. PATENT DOCUMENTS

| | | | |
|---|---|---|---|
| 4,280,964 | A | 7/1981 | Grychtol |
| 5,910,622 | A | 6/1999 | Brodmann et al. |

(Continued)

FOREIGN PATENT DOCUMENTS

| | | |
|---|---|---|
| CN | 107857706 A | 3/2018 |
| CN | 109553904 A | 4/2019 |

(Continued)

OTHER PUBLICATIONS

English text machine translation of Fujii et al. (JP 2012-187840 A) accessed online from Espacenet; PDF pp. 1-38 is attached. (Year: 2012).*
International Search Report issued in International Application No. PCT/JP2020/031883 on Nov. 2, 2020.
Written Opinion of the ISA issued in International Application No. PCT/JP2020/031883 on Nov. 2, 2020.
English language translation of the following: Office action dated Mar. 22, 2023 from the JPO in a Japanese patent application No. 2021-550421 corresponding to the instant patent application.

*Primary Examiner* — Katie L. Hammer
(74) *Attorney, Agent, or Firm* — SOLARIS Intellectual Property Group, PLLC

(57) ABSTRACT

Provided are a textile printing pretreatment liquid including water and an onium salt compound represented by Formula (A) or Formula (B), a textile printing ink set, and an ink jet textile printing method. $R^{A1}$ to $R^{A4}$ and $R^{B1}$ to $R^{B6}$ each represent a hydrocarbon group that may include at least one of an aromatic ring, a hetero ring, —O—, —C(=O)O—, or a substituent. At least one of $R^{A1}$ to $R^{A4}$ and at least one of $R^{B1}$ to $R^{B6}$ include at least one of —O—, —C(=O)O—, —OH, or an allyl group and may include a substituent. $X^+$ represents $N^+$ or $P^+$. $Y^-$ represents a counter anion. L represents a divalent linking group.

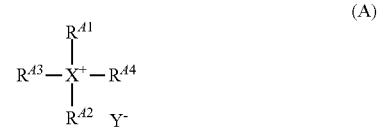

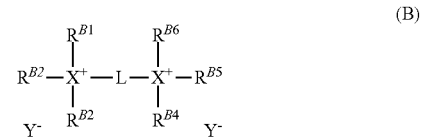

12 Claims, No Drawings

(51) Int. Cl.
  *C09D 11/40* (2014.01)
  *D06P 1/52* (2006.01)
  *D06P 1/66* (2006.01)
  *D06P 5/00* (2006.01)
  *D06P 5/30* (2006.01)

(56) References Cited

U.S. PATENT DOCUMENTS

| | | | |
|---|---|---|---|
| 5,922,625 | A | 7/1999 | Haruta et al. |
| 2004/0194660 | A1* | 10/2004 | Taguchi ................. C09D 11/38 106/31.47 |
| 2014/0186533 | A1* | 7/2014 | Kitagawa ................. D06P 1/66 427/288 |
| 2019/0100037 | A1 | 4/2019 | Taga et al. |
| 2020/0115576 | A1 | 4/2020 | Kodama et al. |

FOREIGN PATENT DOCUMENTS

| | | |
|---|---|---|
| JP | S38-23294 B1 | 11/1963 |
| JP | S52-59786 A | 5/1977 |
| JP | S55-3483 A | 1/1980 |
| JP | S60-9980 A | 1/1985 |
| JP | H07-26474 A | 1/1995 |
| JP | H09-267549 A | 10/1997 |
| JP | H10-052908 | 2/1998 |
| JP | 2002-503294 A | 1/2002 |
| JP | 2012187840 A * | 10/2012 |
| JP | 2018-114751 A | 7/2018 |
| JP | 2018-150401 A | 9/2018 |
| JP | 2019-038893 | 3/2019 |
| JP | 2019-064159 A | 4/2019 |
| WO | 2019/004327 A1 | 1/2019 |

* cited by examiner

TEXTILE PRINTING PRETREATMENT LIQUID, TEXTILE PRINTING INK SET, INK JET TEXTILE PRINTING METHOD, PRINTED TEXTILE, AND ONIUM SALT COMPOUND

CROSS-REFERENCE TO RELATED APPLICATIONS

This application is a continuation application of International Application No. PCT/JP2020/031883, filed Aug. 24, 2020, the disclosure of which is incorporated herein by reference in its entirety. Further, this application claims priority from Japanese Patent Application No. 2019-180625, filed Sep. 30, 2019, the disclosure of which is incorporated herein by reference in their entirety.

BACKGROUND OF THE INVENTION

1. Field of the Invention

The present disclosure relates to a textile printing pretreatment liquid, a textile printing ink set, an ink jet textile printing method, a printed textile, and an onium salt compound.

2. Description of the Related Art

For textile printing such as ink jet textile printing, various studies have been performed in these years.

For example, JP2019-64159A discloses, as an image-forming method that can achieve, in printed matter of a textile, improved fastness to water and that can form an image also on a recording sheet, an image-forming method using aqueous inks to form images on recording media including a textile and a recording sheet; the method includes an image printing step of ejecting the aqueous inks onto such a recording medium by an ink jet process to print an image; in the image printing step, of the aqueous inks, the chromatic color ink employed remains the same irrespective of the type of the recording medium; when the recording medium is the textile, the method further includes a treatment-agent application step of applying a treatment agent onto the textile, and the aqueous inks are aqueous inks that aggregate or thicken upon contact with the treatment agent. JP2019-64159A also discloses using, as the treatment liquid, a treatment liquid including a cationic polymer.

In addition, JP2018-150401A discloses, as a textile printing ink composition that has high preservation stability and high stability of continuous printing, that does not apply, to the head, the load of wiping maintenance for solidified ink and is benign to the printing environment and the printer machine, and that can provide a good printed textile, a textile printing ink composition containing (A) an organic acid having a lactone structure having hydroxy groups as substituents in which one or more hydroxy groups are turned into alkaline salts, (B) a coloring agent, (C) a styrene-(meth)acrylic copolymer, (D) glycerol, and (E) a urethane resin. JP2018-150401A also discloses that fiber to which a textile printing ink composition is to be applied is pretreated by applying an aqueous solution at least including one or more thickening agents, an alkaline substance, a reduction inhibitor, and a hydrotropy agent.

SUMMARY OF THE INVENTION

However, in some cases, there is a demand for a printed textile that is obtained by textile printing such as ink jet textile printing and that has further improved optical density, washing resistance, and texture. The term "washing resistance" means that, even after the printed textile is repeatedly washed, the printed textile is less likely to undergo a decrease in the optical density.

Objects of embodiments of the present disclosure are to provide a textile printing pretreatment liquid, a textile printing ink set, and an ink jet textile printing method that can provide a printed textile having high optical density, high washing resistance, and good texture.

An object of another embodiment of the present disclosure is to provide a printed textile having high optical density, high washing resistance, and good texture.

An object of still another embodiment of the present disclosure is to provide an onium salt compound that is useful as a component in the textile printing pretreatment liquid.

Specific means for achieving the objects include the following embodiments.

<1> A textile printing pretreatment liquid including:
water; and
an onium salt compound represented by Formula (A) below or Formula (B) below.

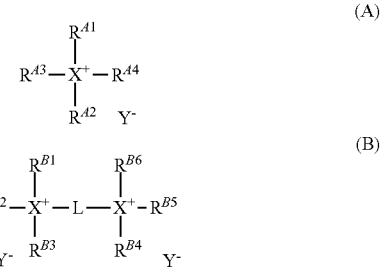

In Formula (A),
$R^{A1}$ to $R^{A4}$ each independently represent a hydrocarbon group that may include at least one of an aromatic ring, a hetero ring, an ether bond, an ester bond, or a substituent,
at least one of $R^{A1}$ to $R^{A4}$ is a hydrocarbon group that includes at least one of an ether bond,
an ester bond, a hydroxy group, or an allyl group and that may include a substituent,
at least two of $R^{A1}$ to $R^{A4}$ may be bonded together to form a ring,
$X^+$ represents an ammonium cation or a phosphonium cation, and
$Y^-$ represents a counter anion,
in Formula (B),
$R^{B1}$ to $R^{B6}$ each independently represent a hydrocarbon group that may include at least one of a hetero ring, an ether bond, an ester bond, or a substituent,
at least one of $R^{B1}$ to $R^{B6}$ is a hydrocarbon group that includes at least one of an ether bond, an ester bond, a hydroxy group, or an allyl group and that may include a substituent,
at least two of $R^{B1}$ to $R^{B6}$ may be bonded together to form a ring,
two $X^+$'s each independently represent an ammonium cation or a phosphonium cation,
two $Y^-$'s each independently represent a counter anion, and
L represents a divalent linking group.

<2> The textile printing pretreatment liquid according to <1>, wherein X⁺ in Formula (A) and two X⁺'s in Formula (B) each independently represent an ammonium cation.
<3> The textile printing pretreatment liquid according to <1> or <2>, wherein at least one of $R^{A1}$ to $R^{A4}$ in Formula (A) and at least one of $R^{B1}$ to $R^{B6}$ in Formula (B) are each a hydrocarbon group that includes an aromatic ring and that may include at least one of a hetero ring, an ether bond, an ester bond, or a substituent.
<4> The textile printing pretreatment liquid according to any one of <1> to <3>, wherein, in the onium salt compound represented by Formula (A) or Formula (B), a cation structure has a molecular weight of 400 or less.
<5> The textile printing pretreatment liquid according to any one of <1> to <4>, wherein a content of the onium salt compound represented by Formula (A) or Formula (B) relative to a total amount of the textile printing pretreatment liquid is 5 mass % to 20 mass %.
<6> A textile printing ink set including:
  the textile printing pretreatment liquid according to any one of <1> to <5>; and
  a textile printing ink containing water and coloring resin particles,
  wherein the coloring resin particles contain an oil-soluble dye and a polymer P including a hydrophilic group.
<7> The textile printing ink set according to <6>, wherein the polymer P further includes a structural unit represented by Formula (1) below and a structural unit represented by Formula (2) below.

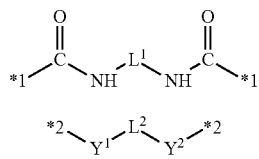

In Formula (1),
$L^1$ represents a hydrocarbon group, and
two *1's each represent a bonding site,
in Formula (2),
$L^2$ represents a hydrocarbon group that has 2 to 50 carbon atoms and that may include an oxygen atom, a nitrogen atom, or a sulfur atom, or a polymer chain that is formed of a polyether chain, a polyester chain, a polycaprolactone chain, a polycarbonate chain, a polybutadiene chain, a polyisoprene chain, or a polyolefin chain and that has a number-average molecular weight of 500 or more,
$Y^1$ and $Y^2$ each independently represent —O—, —S—, or —NRz-,
Rz represents a hydrogen atom or a hydrocarbon group having 1 to 20 carbon atoms, and
two *2's each represent a bonding site.
<8> The textile printing ink set according to <7>, wherein $L^2$ in Formula (2) is a polymer chain that is formed of a polycarbonate chain or a polyether chain and that has a number-average molecular weight of 500 or more.
<9> The textile printing ink set according to any one of <6> to <8>, wherein the polymer P has a glass transition temperature of 50° C. or less.
<10> The textile printing ink set according to any one of <6> to <9>, wherein the hydrophilic group in the polymer P is at least one selected from the group consisting of a carboxy group and a salt of a carboxy group.

<11> The textile printing ink set according to any one of <6> to <10>, wherein the polymer P has a weight-average molecular weight of 8000 to 30000.
<12> The textile printing ink set according to any one of <6> to <11>, wherein the oil-soluble dye includes an azo dye having an ionic group.
<13> An ink jet textile printing method using the textile printing ink set according to any one of <6> to <12>, the method including:
  a step of pretreating a textile by applying the textile printing pretreatment liquid;
  a step of applying the textile printing ink by an ink jet process to the pretreated textile; and
  a step of heat-treating the textile to which the textile printing ink has been applied, to obtain a printed textile.
<14> A printed textile including a textile and an image,
  wherein the image includes an onium salt compound represented by Formula (A) below or Formula (B) below, an oil-soluble dye, and a polymer P including a hydrophilic group.

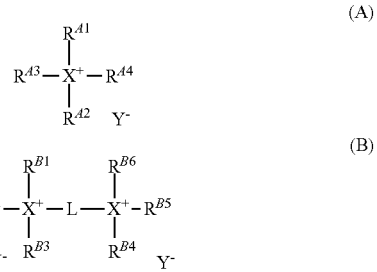

In Formula (A),
  $R^{A1}$ to $R^{A4}$ each independently represent a hydrocarbon group that may include at least one of an aromatic ring, a hetero ring, an ether bond, an ester bond, or a substituent,
  at least one of $R^{A1}$ to $R^{A4}$ is a hydrocarbon group that includes at least one of an ether bond, an ester bond, a hydroxy group, or an allyl group and that may include a substituent,
  at least two of $R^{A1}$ to $R^{A4}$ may be bonded together to form a ring,
  X⁺ represents an ammonium cation or a phosphonium cation, and
  Y⁻ represents a counter anion,
  in Formula (B),
  $R^{B1}$ to $R^{B6}$ each independently represent a hydrocarbon group that may include at least one of a hetero ring, an ether bond, an ester bond, or a substituent,
  at least one of $R^{B1}$ to $R^{B6}$ is a hydrocarbon group that includes at least one of an ether bond, an ester bond, a hydroxy group, or an allyl group and that may include a substituent,
  at least two of $R^{B1}$ to $R^{B6}$ may be bonded together to form a ring,
  two X⁺'s each independently represent an ammonium cation or a phosphonium cation,
  two Y⁻'s each independently represent a counter anion, and
  L represents a divalent linking group.
<15> An onium salt compound represented by Formula (A1) below, Formula (A2) below, Formula (B1) below, or Formula (B2) below.

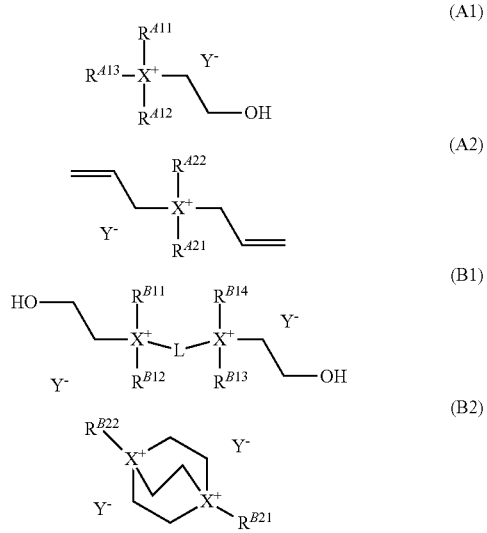

In Formula (A1),
$R^{A11}$ to $R^{A13}$ each independently represent a hydrocarbon group that may include at least one of a hetero ring, an ether bond, an ester bond, or a substituent,
at least two of $R^{A11}$ to $R^{A13}$ may be bonded together to form a ring,
$X^+$ represents an ammonium cation or a phosphonium cation, and
$Y^-$ represents a counter anion,
in Formula (A2),
$R^{A21}$ represents an alkyl group having 1 to 4 carbon atoms or an aryl group,
$R^{A22}$ represents an alkyl group having 8 to 18 carbon atoms,
$X^+$ represents an ammonium cation or a phosphonium cation, and
$Y^-$ represents a counter anion,
in Formula (B1),
$R^{B11}$ to $R^{B14}$ each independently represent a hydrocarbon group that may include at least one of a hetero ring, an ether bond, an ester bond, or a substituent,
$R^{B11}$ and $R^{B12}$ may be bonded together to form a ring,
$R^{B13}$ and $R^{B14}$ may be bonded together to form a ring,
L represents an alkyl group having 4 to 18 carbon atoms, an arylene group, or a divalent linking group formed by bonding together an arylene group and an alkyl group having 4 to 18 carbon atoms,
two $X^+$'s each independently represent an ammonium cation or a phosphonium cation, and
two $Y^-$'s each independently represent a counter anion,
in Formula (B2),
$R^{B21}$ and $R^{B22}$ each independently represent a hydrocarbon group that may include at least one of a hetero ring, an ether bond, an ester bond, or a substituent,
at least one of $R^{B21}$ or $R^{B22}$ is a hydrocarbon group that includes at least one of an ether bond, an ester bond, a hydroxy group, or an allyl group and that may include a substituent,
two $X^+$'s each independently represent an ammonium cation or a phosphonium cation, and
two $Y^-$'s each independently represent a counter anion.

Embodiments of the present disclosure provide a textile printing pretreatment liquid, a textile printing ink set, and an ink jet textile printing method that can provide a printed textile that has high optical density, high washing resistance, and good texture.

Another embodiment of the present disclosure provides a printed textile that has high optical density, high washing resistance, and good texture.

Still another embodiment of the present disclosure provides an onium salt compound that is useful as a component in the textile printing pretreatment liquid.

DESCRIPTION OF THE PREFERRED EMBODIMENTS

In the present disclosure, numerical ranges described as "a value 'to' another value" mean ranges including the value and the other value respectively as the minimum value and the maximum value.

In the present disclosure, the amount of each of components in a composition means, when the composition contains a plurality of substances belonging to such a component, the total amount of the plurality of substances in the composition unless otherwise specified.

In the present disclosure, among numerical ranges described in series, the upper limit value or the lower limit value of a numerical range may be replaced by the upper limit value or the lower limit value of one of other numerical ranges described in series, or may be replaced by a value described in Examples.

In the present disclosure, the term "step" includes not only an independent step, but also a step that is not clearly distinguished from another step but that achieves the intended result of the step.

In the present disclosure, "image" is a general term for films (including coating films) formed from textile printing inks.

In the present disclosure, the concept of "image" also encompasses solid images (solid images).

Textile Printing Pretreatment Liquid

The textile printing pretreatment liquid according to the present disclosure (hereafter, also simply referred to as "pretreatment liquid") contains water and an onium salt compound represented by Formula (A) or Formula (B) described later (hereafter, also referred to as "specified onium salt compound").

The textile printing is performed by applying, to a textile, an ink containing water and a dye (for example, a specified ink in an ink set described later) to form an image. The textile on which the image has been formed will be referred to as a printed textile.

In this textile printing, a textile to which the ink is to be applied is pretreated using the pretreatment liquid according to the present disclosure, to thereby provide a printed textile that has high optical density, high washing resistance, and good texture.

The reasons why such advantages are provided are inferred as follows.

The specified onium salt compound in the pretreatment liquid according to the present disclosure is, unlike cationic polymers used in existing pretreatment liquids, a low-molecular-weight compound (refer to Formula (A) and Formula (B) described later) and hence has high mobility. For this reason, in the case of applying an ink to a textile pretreated with the pretreatment liquid according to the present disclosure, in the surface layer region of the textile, considerable opportunity of the interaction between the specified onium salt compound and the dye is inferentially ensured.

In addition, the specified onium salt compound includes at least one of an ether bond, an ester bond, a hydroxy group, or an allyl group (refer to descriptions of Formula (A) below and Formula (B) below), so that the interaction between the dye and the specified onium salt compound inferentially becomes stronger.

For these reasons, in the case of performing textile printing on a textile pretreated with the pretreatment liquid according to the present disclosure, the dye can be aggregated and firmly fixed in the surface layer region of the textile, to thereby inferentially provide a printed textile having high optical density and high washing resistance.

In addition, since the specified onium salt compound in the pretreatment liquid is a low-molecular-weight compound, compared with the cases of using existing pretreatment liquids containing cationic polymers, a printed textile that has good texture (in particular, softness) is inferentially provided.

Water

The pretreatment liquid according to the present disclosure contains water.

The water content of the pretreatment liquid according to the present disclosure relative to the total amount of the pretreatment liquid is, for example, 40 mass % or more, preferably 50 mass % or more, still more preferably 60 mass % or more, still more preferably 80 mass % or more.

The upper limit of the water content, though it depends on, for example, the amount of the specified onium salt compound, is, relative to the total amount of the pretreatment liquid, for example, 98 mass % or less, preferably 95 mass % or less.

Specified Onium Salt Compound

The pretreatment liquid according to the present disclosure contains a specified onium salt compound.

The pretreatment liquid contains a single specified onium salt compound alone or two or more specified onium salt compounds.

The specified onium salt compound is an onium salt compound represented by Formula (A) below or Formula (B) below (hereafter, also referred to as "compound represented by Formula (A) or Formula (B)").

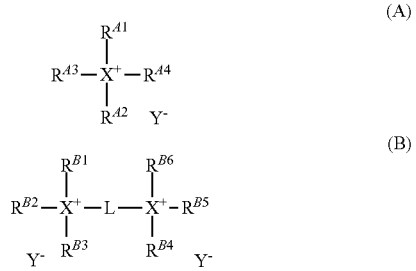

In Formula (A),
$R^{A1}$ to $R^{A4}$ each independently represent a hydrocarbon group that may include at least one of an aromatic ring, a hetero ring, an ether bond (specifically, —O—), an ester bond (specifically, —C(=O)O—), or a substituent,
at least one of $R^{A1}$ to $R^{A4}$ is a hydrocarbon group that includes at least one of an ether bond, an ester bond, a hydroxy group, or an allyl group and that may include a substituent,
at least two of $R^{A1}$ to $R^{A4}$ may be bonded together to form a ring, $X^+$ represents an ammonium cation or a phosphonium cation, and
$Y^-$ represents a counter anion.

In Formula (B),
$R^{B1}$ to $R^{B6}$ each independently represent a hydrocarbon group that may include at least one of a hetero ring, an ether bond, an ester bond, or a substituent,
at least one of $R^{B1}$ to $R^{B6}$ is a hydrocarbon group that includes at least one of an ether bond, an ester bond, a hydroxy group, or an allyl group and that may include a substituent,
at least two of $R^{B1}$ to $R^{B6}$ may be bonded together to form a ring,
two $X^+$'s each independently represent an ammonium cation or a phosphonium cation,
two $Y^-$'s each independently represent a counter anion, and
L represents a divalent linking group.

In Formula (A), $R^{A1}$ to $R^{A4}$ each independently represent a hydrocarbon group that may include at least one of an aromatic ring, a hetero ring, an ether bond (specifically, —O—), an ester bond (specifically, —C(=O)O—), or a substituent.

In other words, the hydrocarbon groups represented by $R^{A1}$ to $R^{A4}$ include carbon atoms and hydrogen atoms and may include heteroatoms such as oxygen atoms.

In Formula (A), examples of the aromatic ring that may be included in the hydrocarbon groups represented by $R^{A1}$ to $R^{A4}$ include a benzene ring, a naphthalene ring, and an anthracene ring. The aromatic ring is preferably a benzene ring.

The form of the aromatic ring in such a hydrocarbon group may be the form of a monovalent aromatic group (specifically, an aryl group), the form of a divalent aromatic group (specifically, an arylene group), or the form of tri- or higher valent aromatic group.

In Formula (A), the hetero ring that may be included in the hydrocarbon groups represented by $R^{A1}$ to $R^{A4}$ may be a hetero ring that includes, as a heteroatom, at least one species of a nitrogen atom, an oxygen atom, or a sulfur atom. The hetero ring may include two or more heteroatoms of the same species.

The hetero ring may be a heteroaromatic ring or a heteroaliphatic ring.

The hetero ring is preferably a five-membered ring to an eight-membered ring, more preferably a five-membered ring or a six-membered ring.

The form of the hetero ring in such a hydrocarbon group may be the form of a monovalent heterocyclic group or the form of a di- or higher valent heterocyclic group.

In Formula (A), examples of the substituent that may be included in the hydrocarbon groups represented by $R^{A1}$ to $R^{A4}$ include a hydroxy group, an amino group, and halogen atoms.

In Formula (A), the total number of carbon atoms of each of $R^{A1}$ to $R^{A4}$ is preferably 1 to 30, more preferably 1 to 20, still more preferably 1 to 12.

Preferably, $R^{A1}$ to $R^{A4}$ each independently represent
an alkyl group that may be substituted with a substituent (a) that is an aryl group, a monovalent heterocyclic group, a hydroxy group, or an amino group,
an alkenyl group that may be substituted with the substituent (a),
an aryl group that may be substituted with the substituent (a),
an alkoxyalkyl group that may be substituted with the substituent (a), an alkylcarbonylalkyl group that may be substituted with the substituent (a), an alkylcarbonyloxyalkyl group that may be substituted with the substituent (a), an alkoxycarbonylalkyl group that may be substituted with the substituent (a), or an alkoxycarbonyloxyalkyl group that may be substituted with the substituent (a).

At least two (preferably two or three) of $R^{A1}$ to $R^{A4}$ may be bonded together to form a ring.

At least one of $R^{A1}$ to $R^{A4}$ is a hydrocarbon group that includes at least one of an ether bond, an ester bond, a hydroxy group, or an allyl group and that may include a substituent.

This provides a stronger interaction between the specified onium salt compound and the dye in the ink, to improve the optical density and the washing resistance of the printed textile.

As at least one of $R^{A1}$ to $R^{A4}$, the "hydrocarbon group that includes at least one of an ether bond, an ester bond, a hydroxy group, or an allyl group and that may include a substituent" is preferably, a hydroxyalkyl group, an allyl group, an alkoxyalkyl group, an alkylcarbonylalkyl group, an alkylcarbonyloxyalkyl group, an alkoxycarbonylalkyl group, or an alkoxycarbonyloxyalkyl group.

As at least one of $R^{A1}$ to $R^{A4}$, the "hydrocarbon group that includes at least one of an ether bond, an ester bond, a hydroxy group, or an allyl group and that may include a substituent" is more preferably, a hydroxyalkyl group having 1 to 12 carbon atoms (still more preferably 1 to 6 carbon atoms), an allyl group, an alkoxyalkyl group having 2 to 12 carbon atoms (still more preferably 2 to 6 carbon atoms), an alkylcarbonylalkyl group having 3 to 12 carbon atoms (still more preferably 3 to 6 carbon atoms), an alkylcarbonyloxyalkyl group having 3 to 12 carbon atoms (still more preferably 3 to 6 carbon atoms), an alkoxycarbonylalkyl group having 3 to 12 carbon atoms (still more preferably 3 to 6 carbon atoms), or, an alkoxycarbonyloxyalkyl group having 3 to 12 carbon atoms (still more preferably 3 to 6 carbon atoms).

At least one of $R^{A1}$ to $R^{A4}$ is preferably a hydrocarbon group that includes an aromatic ring and that may include at least one of a hetero ring, an ether bond, an ester bond, or a substituent.

This provides an even stronger interaction between the specified onium salt compound and the dye in the ink, to further improve the optical density and the washing resistance of the printed textile.

As at least one of $R^{A1}$ to $R^{A4}$, the "hydrocarbon group that includes an aromatic ring and that may include at least one of a hetero ring, an ether bond, an ester bond, or a substituent" is preferably, a phenyl group, a benzyl group, a phenoxy group, a benzyloxy group, a phenylcarbonyl group, a phenoxyalkyl group having 7 to 12 carbon atoms, a benzyloxyalkyl group having 7 to 12 carbon atoms, a phenylcarbonylalkyl group having 8 to 12 carbon atoms, or a diphenylmethyloxyalkyl group having 14 to 20 carbon atoms.

In Formula (A), $X^+$ represents an ammonium cation (specifically, $N^+$) or a phosphonium cation (specifically, $P^+$).

From the viewpoint of further improving the optical density and the washing resistance of the printed textile, $X^+$ in Formula (A) is preferably an ammonium cation.

In Formula (A), $Y^-$ represents a counter anion.

Examples of the counter anion represented by $Y^-$ include;

halide ions such as $Cl^-$, $Br^-$, and $I^-$;

an organic sulfonate anion having a substituent selected from the group consisting of alkyl groups, alkenyl groups, alkynyl groups, cycloalkyl groups, alkoxy groups, aryl groups, aralkyl groups, and heterocyclic groups;

$PF_6^-$; and $BF_4^-$.

The counter anion represented by $Y^-$ is, from the viewpoint of solubility in the pretreatment liquid, preferably $Cl^-$, $Br^-$, or a sulfonate anion having an alkyl group, still more preferably $Cl^-$ or $Br^-$, still more preferably $Cl^-$.

In Formula (B), the groups represented by $R^{B1}$ to $R^{B6}$ have the same definition and preferred examples as in the groups represented by $R^{A1}$ to $R^{A4}$ in Formula (A).

In Formula (B), at least one of $R^{B1}$ to $R^{B6}$ is a hydrocarbon group that includes at least one of an ether bond, an ester bond, a hydroxy group, or an allyl group and that may include a substituent. This provides a stronger interaction between the specified onium salt compound and the dye in the ink, to improve the optical density and the washing resistance of the printed textile.

Preferred examples of, as at least one of $R^{B1}$ to $R^{B6}$, the "hydrocarbon group that includes at least one of an ether bond, an ester bond, a hydroxy group, or an allyl group and that may include a substituent" are the same as the preferred examples of, as at least one of $R^{A1}$ to $R^{A4}$, the "hydrocarbon group that includes at least one of an ether bond, an ester bond, a hydroxy group, or an allyl group and that may include a substituent".

At least one of $R^{B1}$ to $R^{B6}$ is preferably a hydrocarbon group that includes an aromatic ring and that may include at least one of a hetero ring, an ether bond, an ester bond, or a substituent. This provides an even stronger interaction between the specified onium salt compound and the dye in the ink, to further improve the optical density and the washing resistance of the printed textile.

Preferred examples of, optionally as at least one of $R^{B1}$ to $R^{B6}$, the "hydrocarbon group that includes an aromatic ring and that may include at least one of a hetero ring, an ether bond, an ester bond, or a substituent" are the same as the preferred examples of, optionally as at least one of $R^{A1}$ to $R^{A4}$, the "hydrocarbon group that includes an aromatic ring and that may include at least one of a hetero ring, an ether bond, an ester bond, or a substituent".

At least two of $R^{B1}$ to $R^{B6}$ may be bonded together to form a ring.

In the case of forming a ring, preferred forms include a form in which at least two of $R^{B1}$ to $R^{B3}$ are bonded together to form a ring, a form in which at least two of $R^{B4}$ to $R^{B6}$ are bonded together to form a ring, a form in which one of $R^{B1}$ to $R^{B3}$ and one of $R^{B4}$ to $R^{B6}$ are bonded together to form a ring, and a form in which two of $R^{B1}$ to $R^{B3}$ and two of $R^{B4}$ to $R^{B6}$ are individually bonded together to form rings.

In Formula (B), two $X^+$'s may be the same or different.

In Formula (B), two $X^+$'s each have the same definition and preferred examples as in $X^+$ in Formula (A).

In Formula (B), two $Y^-$'s may be the same or different.

In Formula (B), two $Y^-$'s each have the same definition and preferred examples as in $Y^-$ in Formula (A).

In Formula (B), L represents a divalent linking group.

The divalent linking group represented by L,
is preferably a divalent organic group constituted by non-metallic atoms,
preferably a divalent organic group constituted by 1 to 60 carbon atoms, 0 to 10 nitrogen atoms, 0 to 50 oxygen atoms, 1 to 100 hydrogen atoms, and 0 to 20 sulfur atoms.

The divalent linking group represented by L is still more preferably,
a single divalent linking group species selected from the group L1 consisting of
an alkylene group,
an ether group (specifically, an ether bond (—O—)),
an ester group (specifically, an ester bond (—C(=O)O—)),
a thioether group (specifically, a thioether bond (—S—)),
a sulfonyl group,
a carbonyl group,
an imino group (specifically, a —NR— group; R represents a hydrogen atom or an alkyl group),
a phenylene group,
a naphthylene group, and
an anthracenylene group; or;
a divalent linking group formed by bonding together two or more species selected from the above-described group L1.

The number of the carbon atoms of the divalent linking group represented by L is not particularly limited.

For example, when L is an ether group, a thioether group, or an unsubstituted imino group, the divalent linking group represented by L has 0 carbon atoms.

From the viewpoint of further improving the optical density and the washing resistance of the printed textile, the divalent linking group represented by L preferably has 10 or less, more preferably 6 or less, still more preferably 4 or less carbon atoms.

In the specified onium salt compound (specifically, the onium salt compound represented by Formula (A) or Formula (B)), the cation structure preferably has a molecular weight of 1000 or less, more preferably has a molecular weight of 700 or less, still more preferably has a molecular weight of 400 or less.

This provides even higher mobility of the specified onium salt compound, to further improve the optical density and the washing resistance of the printed textile.

In the specified onium salt compound (specifically, the onium salt compound represented by Formula (A) or Formula (B)), the cation structure is the following cation structure (AC) or the following cation structure (BC).

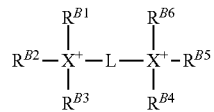

(BC)

The meanings of the symbols in the cation structure (AC) and cation structure (BC) below are the same as the meanings of the symbols in Formula (A) and Formula (B).

In the specified onium salt compound, the cation structure preferably has a C log P of −3 or more and 6 or less.

In the specified onium salt compound, the cation structure more preferably has a C log P of −2 or more and 5 or less, still more preferably −1 or more and 5 or less.

When the C log P is 6 or less, the printed textile has further improved optical density.

When the C log P is −3 or more, the printed textile has further improved washing resistance.

"C log P" is a parameter indicating the hydrophobicity of a compound. The higher the C log P, the higher the hydrophobicity of the compound.

C log P is the calculated value of the common logarithm log P of 1-octanol/water partition coefficient P. As the method and software used for calculation of C log P, publicly known methods and software are applicable.

In the present disclosure, C log P means a value determined using the C log P program included n ChemBioDraw Ultra 12.0 from Cambridge soft Corporation.

The specified onium salt compound (specifically, the onium salt compound represented by Formula (A) or Formula (B)) is, from the viewpoint of further improving the optical density and the washing resistance of the printed textile to be formed, particularly preferably the onium salt compound represented by Formula (B).

Specific examples of the specified onium salt compound (specifically, the onium salt compound represented by Formula (A) or Formula (B)) are Compound O-1 to O-28 in EXAMPLES described later. However, the specified onium salt compound is not limited to these specific examples.

The content of the specified onium salt compound relative to the total amount of the textile printing pretreatment liquid is preferably 2 mass % to 25 mass %, more preferably 5 mass % to 20 mass %, still more preferably 5 mass % to 15 mass %.

When the content of the specified onium salt compound relative to the total amount of the textile printing pretreatment liquid is 2 mass % or more, the printed textile to be formed has further improved washing resistance.

When the content of the specified onium salt compound relative to the total amount of the textile printing pretreatment liquid is 25 mass % or less, the printed textile to be formed has further improved texture.

Specific Forms of Specified Onium Salt Compound

More specific forms of the specified onium salt compound (specifically, the onium salt compound represented by Formula (A) or Formula (B)) include onium salt compounds represented by the following Formula (A1), the following Formula (A2), the following Formula (B1), or the following Formula (B2).

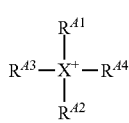

(AC)

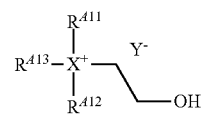

(A1)

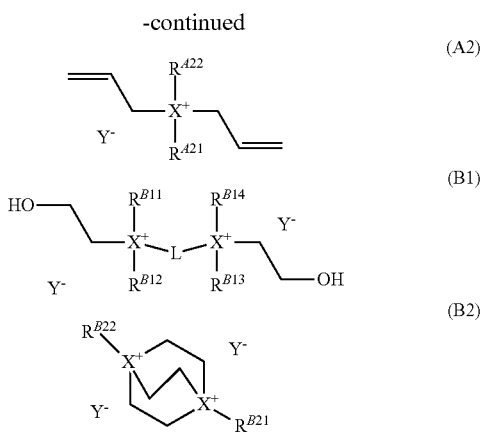

In Formula (A1),
$R^{A11}$ to $R^{A13}$ each independently represent a hydrocarbon group that may include at least one of an aromatic ring, a hetero ring, an ether bond, an ester bond, or a substituent,
at least two of $R^{A11}$ to $R^{A13}$ may be bonded together to form a ring,
$X^+$ represents an ammonium cation or a phosphonium cation, and
$Y^-$ represents a counter anion.
In Formula (A2),
$R^{A21}$ represents an alkyl group having 1 to 4 carbon atoms or an aryl group,
$R^{A22}$ represents an alkyl group having 8 to 18 carbon atoms,
$X^+$ represents an ammonium cation or a phosphonium cation, and
$Y^-$ represents a counter anion.
In Formula (B1),
$R^{B11}$ to $R^{B14}$ each independently represent a hydrocarbon group that may include at least one of an aromatic ring, a hetero ring, an ether bond, an ester bond, or a substituent,
$R^{B11}$ and $R^{B12}$ may be bonded together to form a ring,
$R^{B13}$ and $R^{B14}$ may be bonded together to form a ring,
L represents an alkyl group having 4 to 18 carbon atoms, an arylene group, or a divalent linking group formed by bonding together an arylene group and an alkyl group having 4 to 18 carbon atoms,
two $X^+$'s each independently represent an ammonium cation or a phosphonium cation, and
two $Y^-$'s each independently represent a counter anion.
In Formula (B2),
$R^{B21}$ and $R^{B22}$ each independently represent a hydrocarbon group that may include at least one of a hetero ring, an ether bond, an ester bond, or a substituent,
at least one of $R^{B21}$ or $R^{B22}$ is a hydrocarbon group that includes at least one of an ether bond,
an ester bond, a hydroxy group, or an allyl group and that may include a substituent,
two $X^+$'s each independently represent an ammonium cation or a phosphonium cation, and
two $Y^-$'s each independently represent a counter anion.

The onium salt compound represented by Formula (A1) is a compound in which, in the onium salt compound represented by Formula (A), one of $R^{A1}$ to $R^{A4}$ is limited to a hydroxyethyl group.

Thus, as preferred examples of the onium salt compound represented by Formula (A1) (for example, preferred forms of the groups, preferred molecular weights, and preferred C log P), preferred examples of the onium salt compound represented by Formula (A) are applicable.

The onium salt compound represented by Formula (A2) is a compound in which, in the onium salt compound represented by Formula (A), two of $R^{A1}$ to $R^{A4}$ are limited to allyl groups.

Thus, as preferred examples of the onium salt compound represented by Formula (A2) (for example, preferred forms of the groups, preferred molecular weights, and preferred C log P), preferred examples of the onium salt compound represented by Formula (A) are applicable.

The onium salt compound represented by Formula (B1) is a compound in which, in the onium salt compound represented by Formula (B), one of $R^{B1}$ to $R^{B3}$ is limited to a hydroxyethyl group and one of $R^{B4}$ to $R^{B6}$ is limited to a hydroxyethyl group.

Thus, as preferred examples of the onium salt compound represented by Formula (B1) (for example, preferred forms of the groups, preferred molecular weights, and preferred C log P), preferred examples of the onium salt compound represented by Formula (B) are applicable.

The onium salt compound represented by Formula (B2) is a compound in which, in the onium salt compound represented by Formula (B),
two of $R^{B1}$ to $R^{B3}$ are limited to methyl groups,
two of $R^{B4}$ to $R^{B6}$ are limited to methyl groups,
the methyl groups serving as two of $R^{B1}$ to $R^{B3}$ and the methyl groups serving as two of $R^{B4}$ to $R^{B6}$ are individually limited to the forms of being bonded together to form rings, and
L is limited to an ethylene group.

Thus, as preferred examples of the onium salt compound represented by Formula (B2) (for example, preferred forms of the groups, preferred molecular weights, and preferred C log P), preferred examples of the onium salt compound represented by Formula (B) are applicable.

Aqueous Organic Solvent

The pretreatment liquid according to the present disclosure may contain at least one aqueous organic solvent.

In the aqueous organic solvent, "aqueous" means that the amount of the solvent soluble in 100 g of distilled water at 25° C. is more than 1 g.

The amount of the aqueous organic solvent soluble is preferably 5 g or more, more preferably 10 g or more, still more preferably 20 g or more.

Examples of the aqueous organic solvent include alcohol-based solvents, amide-based solvents, nitrile-based solvents, polyalkylene glycol-based solvents, and polyalkylene glycol alkyl ether-based solvents; preferred are alcohol-based solvents and amide-based solvents.

Examples of the aqueous organic solvent include methanol, ethanol, n-propanol, isopropanol, n-butanol, isobutanol, tert-butanol, trimethylolpropane, ethylene glycol, diethylene glycol, triethylene glycol, tetraethylene glycol, propylene glycol, 2-methyl-1,3-propanediol, butylene glycol, 1,2,6-hexanetriol, thioglycol, hexylene glycol, glycerol, diglycerol, 2-pyrrolidone, N-methyl-2-pyrrolidone, 1,5-pentanediol, 1,6-hexanediol, ethylene glycol monoethyl ether, ethylene glycol monobutyl ether, acetonitrile, polyethylene glycol (for example, molecular weight: 400 to 800), hydroxyethylpyrrolidone, hydroxypropylpyrrolidone, valerolactam, caprolactam, heptalactam, polyethylene glycol monomethyl ether (molecular weight: 400), polyethylene glycol monomethyl ether (molecular weight: 550), polyethylene glycol dimethyl ether (molecular weight: 500), tripropylene glycol, tetrapropylene glycol, polypropylene glycol (molecular weight: 400), polypropylene glycol (molecular weight: 600), and polypropylene glycol (molecular weight: 700).

The aqueous organic solvent preferably includes
at least one selected from the group consisting of trimethylolpropane, ethylene glycol, diethylene glycol, triethylene glycol, tetraethylene glycol, propylene glycol, 2-methyl-1,3-propanediol, glycerol, 2-pyrrolidone, 1,5-pentanediol, 1,6-hexanediol, and ethylene glycol monobutyl ether,
more preferably includes at least one selected from the group consisting of ethylene glycol, diethylene glycol, triethylene glycol, tetraethylene glycol, propylene glycol, 2-methyl-1,3-propanediol, glycerol, 2-pyrrolidone, and ethylene glycol monobutyl ether,
still more preferably includes at least one selected from the group consisting of ethylene glycol, glycerol, 2-methyl-1,3-propanediol, 2-pyrrolidone, and tetraethylene glycol.

When the pretreatment liquid contains an aqueous organic solvent, the content of the aqueous organic solvent in the pretreatment liquid relative to the total amount of the pretreatment liquid is preferably 1 mass % to 50 mass %, more preferably 2 mass % to 30 mass %, still more preferably 3 mass % to 20 mass %, still more preferably 5 mass % to 15 mass %.

Surfactant

The pretreatment liquid according to the present disclosure may contain at least one surfactant.

The surfactant is not particularly limited, and publicly known surfactants such as silicone-based surfactants, fluorosurfactants, and acetylene glycol-based surfactants are usable.

When the pretreatment liquid according to the present disclosure contains a surfactant, the surfactant content relative to the total amount of the pretreatment liquid is preferably 0.05 mass % to 2.0 mass %, more preferably 0.1 mass % to 2.0 mass %.

Other Aggregation Agent

The above-described specified onium salt compound functions as an aggregation agent for aggregating the dye in the ink.

The pretreatment liquid according to the present disclosure may contain, in addition to the above-described specified onium salt compound, at least one other aggregation agent.

Examples of the other aggregation agent include polyvalent metallic salts and cationic compounds.

Polyvalent Metallic Salts

The polyvalent metallic salts are compounds constituted by a di- or higher valent metallic ion and an anion.

Specific examples include calcium chloride, calcium nitrate, calcium sulfate, calcium acetate, calcium hydroxide, calcium carbonate, magnesium chloride, magnesium acetate, magnesium sulfate, magnesium carbonate, barium sulfate, barium chloride, zinc sulfide, zinc carbonate, and copper nitrate.

Cationic Compounds

The cationic compounds are not particularly limited and may be low-molecular-weight compounds or high-molecular-weight compounds.

Examples of the low-molecular-weight cationic compounds include (2-hydroxyethyl)trimethylammonium chloride, benzoylcholine chloride, benzyltriethylammonium chloride, trimethylacetohydrazide ammonium chloride, 1-butyl-1-methylpyrrolidinium chloride, 3-hydroxy-4-(trimethylammmonio)butyrate hydrochloric acid salt, glycidyltrimethylammonium chloride, L-carnitine hydrochloric acid salt, and $C_{6-30}$ alkylcarbonyloxyethyltrimethyl ammonium chloride.

Examples of the high-molecular-weight cationic compounds include cationic polymers that are soluble in water and are positively charged in water, such as polyallylamine or derivatives thereof, amine-epihalohydrin copolymers, and other quaternary ammonium salt-type cationic polymers. Note that, depending on the case, a water-dispersible cationic polymer may also be used.

Other Component

The pretreatment liquid according to the present disclosure may contain, in addition to the above-described components, another component.

Examples of the other component include a pH adjusting agent, a fluorescent brightening agent, a surface tension modifier, an anti-foaming agent, an anti-drying agent, a lubricant, a thickener, an ultraviolet absorbent, an anti-fading agent, an antistatic agent, a matting agent, an antioxidant, a resistivity control agent, an anticorrosive, a reduction inhibitor, a preservative, a fungicide, and a chelating agent.

Textile Printing Ink Set

A textile printing ink set according to the present disclosure (hereafter, also simply referred to as "ink set") includes
the above-described textile printing pretreatment liquid according to the present disclosure, and
a textile printing ink containing water and coloring resin particles (hereafter, also referred to as "specified ink").

The coloring resin particles in the specified ink contain an oil-soluble dye and a polymer P including a hydrophilic group.

The ink set according to the present disclosure includes the above-described textile printing pretreatment liquid according to the present disclosure.

For this reason, the ink set according to the present disclosure provides a printed textile that has high optical density, high washing resistance, and good texture.

In particular, the ink set according to the present disclosure employs the specified ink, to thereby more effectively exert the above-described effect of the textile printing pretreatment liquid according to the present disclosure.

The reason for this is inferred as follows.

In the specified ink, the polymer P contained in the coloring resin particles, in the specified ink to be applied to a textile, due to the action of the hydrophilic group included in the polymer P, inferentially contributes to dispersion stability of the coloring resin particles (specifically, dispersion stability of the oil-soluble dye).

When, to a textile to which a pretreatment liquid has been applied using the pretreatment liquid according to the present disclosure, the specified ink is applied and subsequently heat treatment is performed, inferentially, the coloring resin particles in the specified ink are separated from each other and, in the surface layer region of the textile, the action of the specified onium salt compound causes the oil-soluble dye to aggregate and the polymer P forms a polymer film including the aggregated oil-soluble dye. This inferentially results in, in the surface layer region of the textile, formation of an image having high fixability.

In this way, use of the ink set according to the present disclosure inferentially provides a printed textile that has high optical density, high washing resistance, and good texture.

The ink set according to the present disclosure includes at least the combination of the textile printing pretreatment liquid according to the present disclosure and the specified ink.

The ink set according to the present disclosure may include a single specified ink alone or two or more specified inks. Examples of the specified ink include a black ink, a yellow ink, a magenta ink, and a cyan ink. The ink set according to the present disclosure preferably includes a black ink serving as the specified ink.

The ink set according to the present disclosure may include a single textile printing pretreatment liquid according to the present disclosure alone or two or more textile printing pretreatment liquids according to the present disclosure.

The ink set according to the present disclosure may include, in addition to the textile printing pretreatment liquid according to the present disclosure and the specified ink, another liquid (for example, an ink other than the specified ink).

The textile printing pretreatment liquid according to the present disclosure is the same as that described above.

Hereinafter, the specified ink in the ink set according to the present disclosure will be described.

The specified ink is, from the viewpoint of forming a fine image, preferably an ink jet ink. When the specified ink is an ink jet ink, the textile printing is ink jet textile printing.

However, from the viewpoint of providing the above-described advantages, the specified ink is not necessarily limited to the ink jet ink. The specified ink may be an ink other than the ink jet ink, such as a gravure ink.

Water

The specified ink contains water.

The water content in the specified ink relative to the total amount of the specified ink is, for example, 40 mass % or more, preferably 50 mass % or more, still more preferably 60 mass % or more.

The upper limit of the water content, though it depends on the solid content of the specified ink, is, relative to the total amount of the specified ink, for example, 90 mass %.

Coloring Resin Particles

The specified ink contains at least one species of coloring resin particles.

The coloring resin particles contain at least one oil-soluble dye and a polymer P including a hydrophilic group.

Polymer P

The polymer P is not particularly limited as long as it includes a hydrophilic group.

Hydrophilic Group

The polymer P includes at least one species of a hydrophilic group.

As described above, the hydrophilic group in the polymer P contributes to, in the specified ink to be applied to a textile, dispersion stability of the coloring resin particles.

The hydrophilic group is preferably an anionic group or a nonionic group and, from the viewpoint of providing a strong effect of improving the dispersion stability, preferably an anionic group.

For example, of an anionic group and a nonionic group that have the same molecular weight, the anionic group provides a stronger effect of improving the dispersion stability. Thus, the anionic group (particularly preferably at least one selected from the group consisting of a carboxy group and a salt of a carboxy group), even in the case of having a low molecular weight, can exert sufficiently the effect of improving the dispersion stability.

The nonionic group may be a group having a polyether structure, and is preferably a monovalent group including a polyalkyleneoxy group.

The anionic group may be neutralized or may not be neutralized.

Examples of the unneutralized anionic group include a carboxy group, a sulfo group, a sulfuric acid group, a phosphonic acid group, and a phosphoric acid group.

Examples of the neutralized anionic group include a salt of a carboxy group, a salt of a sulfo group, a salt of a sulfuric acid group, a salt of a phosphonic acid group, and a salt of a phosphoric acid group.

In the present disclosure, the term "neutralized anionic group" means an anionic group in the form of a "salt" (for example, a salt of a carboxy group (for example, —COONa)).

The neutralization can be performed using, for example, an alkali metal hydroxide (for example, sodium hydroxide or potassium hydroxide) or an organic amine (for example, triethylamine).

The hydrophilic group in the polymer P is, from the viewpoint of the dispersion stability, preferably an anionic group,
more preferably at least one species selected from the group consisting of a carboxy group, a salt of a carboxy group, a sulfo group, a salt of a sulfo group, a sulfuric acid group, a salt of a sulfuric acid group, a phosphonic acid group, a salt of a phosphonic acid group, a phosphoric acid group, and a salt of a phosphoric acid group,
still more preferably at least one species selected from the group consisting of a carboxy group and a salt of a carboxy group.

In the above-described salt of a carboxy group, salt of a sulfo group, salt of a sulfuric acid group, salt of a phosphonic acid group, and salt of a phosphoric acid group, "salt" is preferably an alkali metal salt or an organic amine salt, more preferably an alkali metal salt.

In the alkali metal salt, the alkali metal is preferably K or Na.

When the polymer P includes, as the hydrophilic group, an anionic group (for example, at least one species selected from the group consisting of a carboxy group and a salt of a carboxy group), and the total number of millimoles of the anionic group (for example, a carboxy group or a salt of a carboxy group) included in 1 g of the polymer P is defined as the acid value of the polymer P, the acid value of the polymer P is, from the viewpoint of the dispersion stability, preferably 0.10 mmol/g to 2.00 mmol/g, more preferably 0.30 mmol/g to 1.50 mmol/g.

When the polymer P has, as the hydrophilic group, an anionic group, the anionic group in the polymer P preferably has a degree of neutralization of 50% to 100%, more preferably 70% to 90%.

The term "degree of neutralization" is, in the polymer P, a ratio of "the number of neutralized anionic groups" to "the total of the number of unneutralized anionic groups (for example, carboxy groups) and the number of neutralized anionic groups (for example, salts of carboxy groups)" (specifically, ratio [Number of neutralized anionic groups/(Number of unneutralized anionic groups+Number of neutralized anionic groups)]).

The degree of neutralization (%) of the polymer P can be measured by neutralization titration.

Glass Transition Temperature (Tg)

The glass transition temperature (Tg) of the polymer P is, from the viewpoint of further improving the optical density and the washing resistance of the printed textile, preferably 60° C. or less, more preferably 50° C. or less, still more preferably 45° C. or less, still more preferably 40° C. or less.

The lower limit of Tg of the polymer P is not particularly limited; however, the lower limit of Tg is, for example, −50° C. or −40° C.

In the present disclosure, the glass transition temperature (Tg) of the polymer P means a value measured by differential scanning calorimetry (DSC).

Specifically, the glass transition temperature is measured in accordance with a method described in JIS K7121 (1987) or JIS K6240 (2011).

In the present disclosure, the glass transition temperature is the extrapolated glass transition onset temperature (hereafter, also referred to as Tig).

More specifically, the method of measuring the glass transition temperature will be described.

In the case of determining the glass transition temperature, the apparatus is held at a temperature about 50° C. lower than the estimated glass transition temperature until it becomes stable; subsequently, heating is performed at a heating rate of 20° C./min to a temperature about 30° C. higher than the glass transition end temperature, and a differential thermal analysis (DTA) curve or a DSC curve is created.

The extrapolated glass transition onset temperature (Tig), which is the glass transition temperature in the present disclosure, is determined as the temperature at the point of intersection between a straight line extended from the baseline from the lower-temperature side to the higher-temperature side in a DTA curve or a DSC curve, and a tangent drawn at the maximum gradient of the curve in the stepped change region of glass transition.

Weight-Average Molecular Weight (Mw)

The weight-average molecular weight (Mw) of the polymer P is, from the viewpoint of further improving the dispersion stability of the coloring resin particles, preferably 5000 to 50000, more preferably 6000 to 40000, still more preferably 8000 to 30000, still more preferably 10000 to 30000.

In the present disclosure, the weight-average molecular weight (Mw) and the number-average molecular weight (Mn) mean polystyrene-equivalent values calculated by gel permeation chromatography (GPC).

The columns employed are, for example, TSKgel (registered trademark) SuperHZM-H, TSKgel (registered trademark) SuperHZ4000, and TSKgel (registered trademark) SuperHZ200 (all are manufactured by Tosoh Corporation).

Type of Polymer P

The type of the polymer P is not particularly limited.

Examples of the polymer P include urethane resins, acrylic resins, polyester resins, polyether resins, polycaprolactone resins, polycarbonate resins, polybutadiene resins, polyisoprene resins, and polyolefin resins.

Such a term "urethane resin" means a resin including at least one species selected from the group consisting of a urethane bond, a urea bond, and a thiourethane bond.

Thus, the urethane resin may include, in addition to such a bond, for example, a polyether chain, a polyester chain, a polycaprolactone chain, a polycarbonate chain, a polybutadiene chain, a polyisoprene chain, or a polyolefin chain.

From the viewpoint of further improving the optical density, the washing resistance, and the texture of the printed textile, the polymer P is preferably a urethane resin.

From the above-described viewpoint, the more preferred form is a form in which the polymer P includes, a structural unit represented by Formula (1) below (hereafter, also referred to as "Unit (1)"), and a structural unit represented by Formula (2) below (hereafter, also referred to as "Unit (2)").

Structural Unit Represented by Formula (1) (Unit (1))

When the polymer P includes the structural unit represented by Formula (1) below (hereafter, also referred to as "Unit (1)"), the polymer P may include a single species of Unit (1) alone, or may include two or more species of Unit (1).

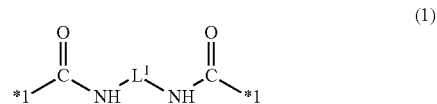

In Formula (1), $L^1$ represents a hydrocarbon group, and two *1's each represent a bonding site.

Unit (1) is preferably bonded to at least the structural unit represented by Formula (2) (hereafter, also referred to as "Unit (2)").

The hydrocarbon group represented by $L^1$ is not particularly limited.

The hydrocarbon group represented by $L^1$ may be a linear hydrocarbon group, may be a hydrocarbon group having a branch, may be a hydrocarbon group including an aromatic ring, or may be a hydrocarbon group including an alicyclic structure.

Examples of the hydrocarbon group represented by L' include a divalent hydrocarbon group being a single species selected from the group P1 consisting of an alkylene group that may include a branched structure and/or an alicyclic structure, an alkylene group that may include a branched structure and/or an alicyclic structure, an alkenylene group that may include a branched structure and/or an alicyclic structure, and an arylene group; and a divalent hydrocarbon group in which two or more species selected from the group P1 are bonded together.

The number of the carbon atoms of the hydrocarbon group represented by $L^1$ is preferably 1 to 20, more preferably 3 to 20, still more preferably 4 to 12.

The compound for forming Unit (1) (hereafter, also referred to as "Unit-(1)-forming compound") may be a diisocyanate compound having a structure in which two moieties "—NH(C=O)—*1" in Unit (1) are each replaced by an isocyanate group (—NCO group).

Specific examples of the Unit-(1)-forming compound are as follows.

However, the Unit-(1)-forming compound is not limited to the following specific examples.

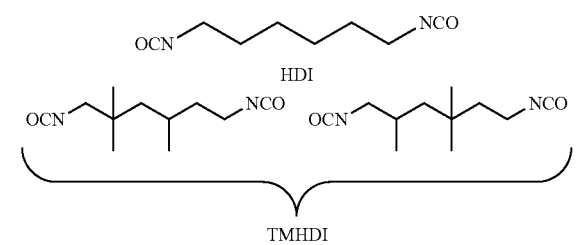

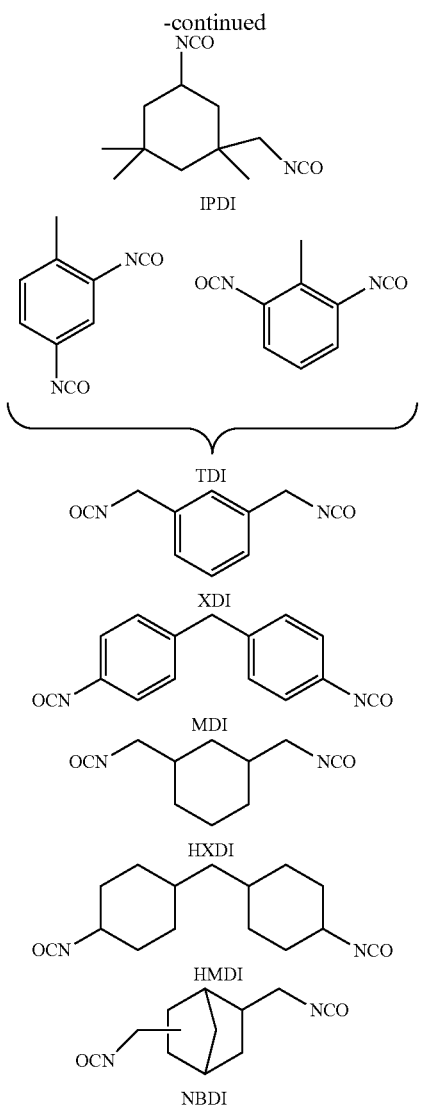

As bifunctional isocyanate compounds, bifunctional isocyanate compounds derived from the above-described specific examples are also usable. Examples include DURANATE (registered trademark) D101, D201, and A101 (manufactured by Asahi Kasei Corporation).

Structural Unit Represented by Formula (2)

When the polymer P includes the structural unit represented by the following Formula (2) (hereafter, also referred to as "Unit (2)"), the polymer P may include a single species of Unit (2) alone, or may include two or more species of Unit (2).

(2)

In Formula (2),

L² represents a hydrocarbon group that has 2 to 50 carbon atoms and that may include an oxygen atom, a nitrogen atom, or a sulfur atom, or a polymer chain that is formed of a polyether chain, a polyester chain, a polycaprolactone chain, a polycarbonate chain, a polybutadiene chain, a polyisoprene chain, or a polyolefin chain and that has a number-average molecular weight of 500 or more, Y¹ and Y² each independently represent —O—, —S—, or —NRz-, Rz represents a hydrogen atom or a hydrocarbon group having 1 to 20 carbon atoms, and two *2's each represent a bonding site.

In the concept of the "hydrocarbon group that has 2 to 50 carbon atoms and that may include an oxygen atom, a nitrogen atom, or a sulfur atom", the hydrocarbon group that has 2 to 50 carbon atoms and that includes an oxygen atom, a nitrogen atom, or a sulfur atom means an organic group having a structure in which, in a hydrocarbon group composed only of carbon atoms and hydrogen atoms, at least one carbon atom is replaced by an oxygen atom, a nitrogen atom, or a sulfur atom, the organic group having 2 to 50 carbon atoms.

As L², the hydrocarbon group that has 2 to 50 carbon atoms and that may include an oxygen atom, a nitrogen atom, or a sulfur atom (hereafter, also simply referred to as "hydrocarbon group represented by L²") is preferably an alkylene group not substituted or having a substituent.

In the alkylene group having a substituent, examples of the substituent include alkoxy groups, alkylcarbonyloxy groups, alkylthio groups, an amino group, monoalkylamino groups, and dialkylamino groups.

Unit (2) is preferably bonded to at least Unit (1).

In Formula (2), the number of carbon atoms of the hydrocarbon group represented by L² is, from the viewpoint of further improving the optical density and the washing resistance of the printed textile, preferably 4 to 50, more preferably 6 to 40.

The hydrocarbon group represented by L² is, from the viewpoint of further improving the optical density and the washing resistance of the printed textile, preferably a chain hydrocarbon group that may include an oxygen atom, a nitrogen atom, or a sulfur atom, and that has a branched structure and 4 to 25 carbon atoms, more preferably an unsubstituted branched alkylene group having 6 to 25 carbon atoms, an alkoxylated branched alkylene group having 6 to 25 carbon atoms (specifically, a branched alkylene group substituted with an alkoxy group), or an alkylcarbonyloxylated branched alkylene group having 6 to 25 carbon atoms (specifically, a branched alkylene group substituted with an alkylcarbonyloxy group).

In the alkoxylated branched alkylene group having 6 to 25 carbon atoms, the number of carbon atoms of the alkoxy group is preferably 1 to 23, more preferably 4 to 22.

In the alkylcarbonyloxylated branched alkylene group having 6 to 25 carbon atoms, the number of carbon atoms of the alkylcarbonyloxy group is preferably 2 to 23, more preferably 6 to 22.

The hydrocarbon group represented by L² is, from the viewpoint of further improving the optical density and the washing resistance of the printed textile, also preferably an alkylene group substituted with a substituent A and having 2 or more carbon atoms.

The substituent A is preferably at least one species selected from the group consisting of a linear alkyl group having 2 or more carbon atoms, a branched alkyl group having 3 or more carbon atoms, a linear alkoxy group having 2 or more carbon atoms, a branched alkoxy group having 3 or more carbon atoms, a linear alkoxyalkyl group having 2 or more carbon atoms, and a branched alkoxyalkyl group having 3 or more carbon atoms.

The polymer chain represented by $L^2$ has a number-average molecular weight (Mn) of 500 or more.

Mn of the polymer chain represented by $L^2$ is preferably 500 to 50000, more preferably 1000 to 40000, still more preferably 1000 to 30000, still more preferably 1000 to 10000, still more preferably 1000 to 5000.

The polymer chain represented by $L^2$ is formed of a polyether chain, a polyester chain, a polycaprolactone chain, a polycarbonate chain, a polybutadiene chain, a polyisoprene chain, or a polyolefin chain.

Examples of the polyether chain include a polyethylene glycol chain, a polypropylene glycol chain, and a polybutylene glycol chain.

The polyester chain may be a residue provided by removing the hydroxy groups at both terminals of Compound (2-17) PEs described later.

The polycaprolactone chain may be a residue provided by removing the hydroxy groups at both terminals of Compound (2-19) PCL described later.

The polycarbonate chain may be a residue provided by removing the hydroxy groups at both terminals of Compound (2-18) PC described later.

$L^2$ is, from the viewpoint of further improving the optical density and the washing resistance of the printed textile, preferably a polymer chain formed of a polycarbonate chain or a polyether chain and having a number-average molecular weight of 500 or more.

The polycarbonate chain preferably includes an alkylene group having 2 to 12 (preferably 3 to 8, more preferably 3 to 6) carbon atoms, still more preferably a residue provided by removing the hydroxy groups at both terminals of Compound (2-18) PC described later.

The polyether chain is preferably a polyethylene glycol chain or a polypropylene glycol chain.

In Formula (2), $Y^1$ and $Y^2$ each independently represent —O—, —S—, or —NRz-, and Rz represents a hydrogen atom or a hydrocarbon group having 1 to 20 carbon atoms.

Rz is preferably a hydrogen atom or an alkyl group having 1 to 10 carbon atoms, more preferably a hydrogen atom or an alkyl group having 1 to 6 carbon atoms, still more preferably a hydrogen atom, a methyl group, or an ethyl group, still more preferably a hydrogen atom.

$Y^1$ and $Y^2$ are each preferably —O— or —S—, more preferably —O—.

The compound for forming Unit (2) (hereafter, also referred to as "Unit-(2)-forming compound") is,
  preferably a compound having a structure in which, in Unit (2), "*2-$Y^1$—" and "—$Y^2$-*2" are each replaced by a hydroxy group, a thiol group, or an amino group (for example, a diol compound, a dithiol compound, or a diamine compound),
  more preferably a diol compound having a structure in which, in Unit (2), "*2-$Y^1$—" and "—$Y^2$-*2" are each replaced by a hydroxy group.

When the Unit-(2)-forming compound is used for forming Unit (2) in which $L^2$ is a polymer chain and is a diol compound, the Unit-(2)-forming compound is a polymer diol.

More specifically, the polymer diol is polyetherdiol, polyesterdiol, polycaprolactonediol, polycarbonatediol, polybutadienediol, polyisoprenediol, or polyolefindiol.

Specific examples of the Unit-(2)-forming compound are as follows.

However, the Unit-(2)-forming compound is not limited to the following specific examples.

(2-1)

(2-2)

(2-3)

(2-4)

(2-5)

(2-6)

(2-7)

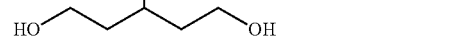
(2-8)

(2-9)

(2-10)

(2-11)

(2-12)

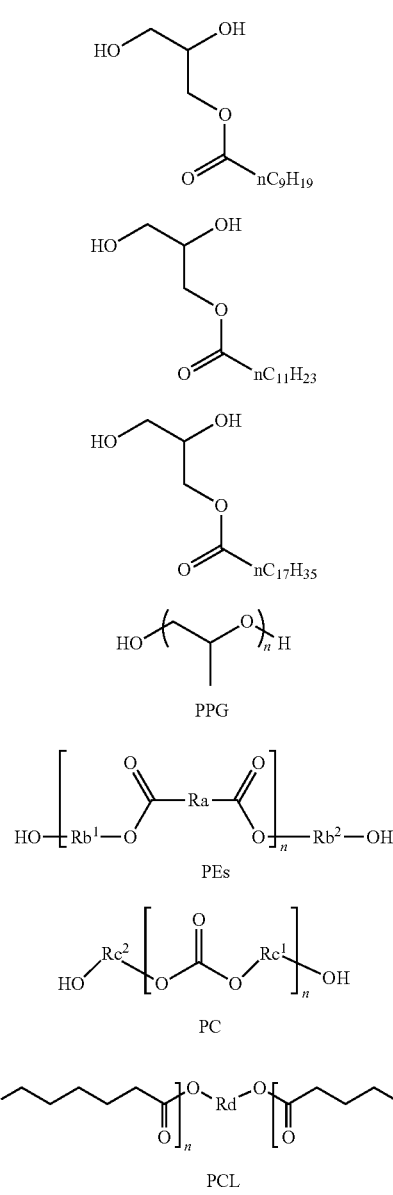

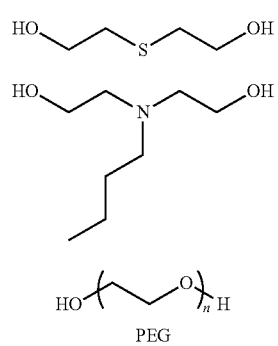

In Compounds (2-12) to (2-15), $nC_7H_{15}$, $nC_9H_{19}$, $nC_{11}H_{23}$, and $nC_{17}H_{35}$ respectively represent a normal heptyl group, a normal nonyl group, a normal undecyl group, and a normal heptadecyl group.

Compound (2-16) PPG is an example of polyetherdiol, polypropylene glycol; n is the repeat number.

Compound (2-17) PEs is polyester diol; n is the repeat number; Ra, $Rb^1$, and $Rb^2$ each independently represent a divalent hydrocarbon group having 2 to 25 carbon atoms. In Compound (2-17) PEs, n Ra's may be the same or different. In Compound (2-17) PEs, n $Rb^1$'s may be the same or different.

Compound (2-18) PC is polycarbonatediol; n is the repeat number; $Rc^1$ and $Rc^2$ each independently represent an alkylene group having 2 to 12 (preferably 3 to 8, more preferably 3 to 6) carbon atoms. In Compound (2-18) PC, n $Rc^1$'s may be the same or different.

Compound (2-19) PCL is polycaprolactonediol; n and m are the repeat numbers; Rd is an alkylene group having 2 to 25 carbon atoms.

Compound (2-22) PEG is an example of polyetherdiol, polyethylene glycol; n is the repeat number.

Examples of the Unit-(2)-forming compound include, in addition to the above-described compounds, the following compounds.

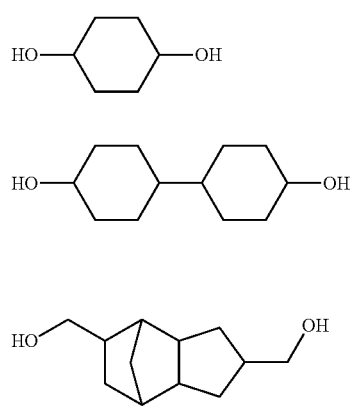

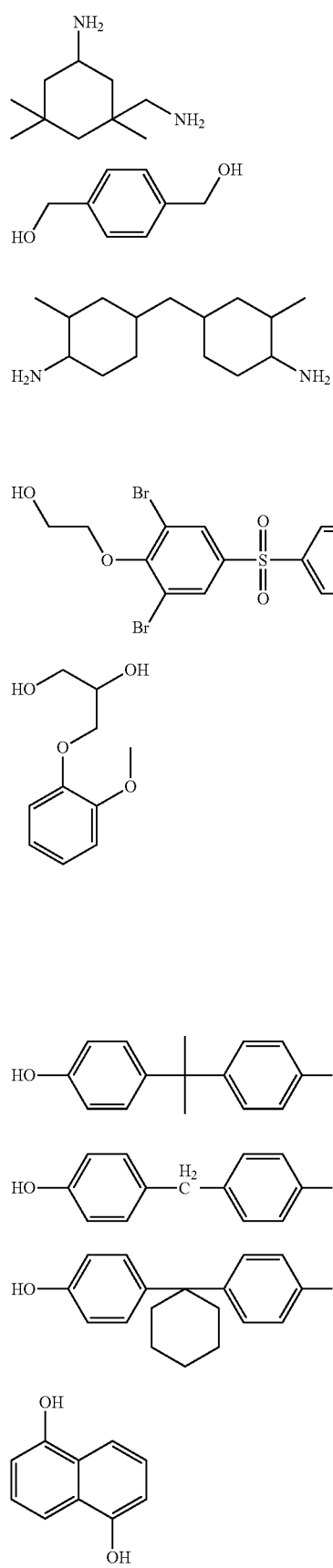

(2-y)
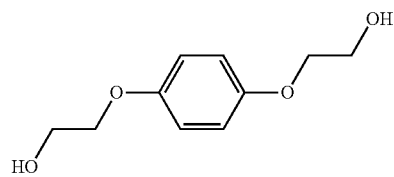
(2-z)
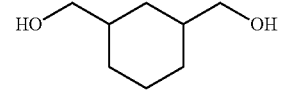
(2-101)
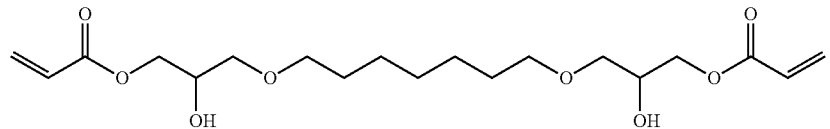
(2-102)
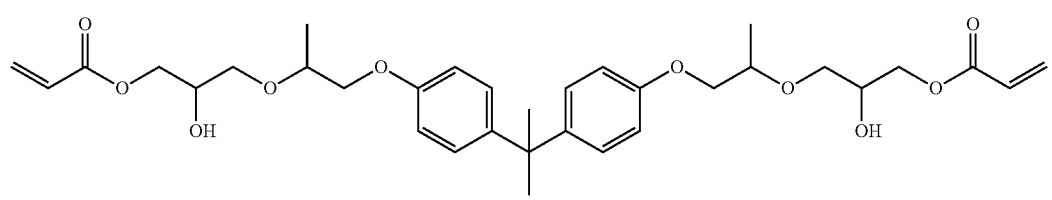
DA-250
(2-103)
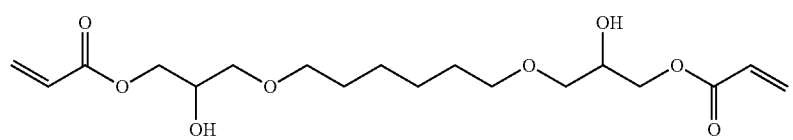
(2-104)
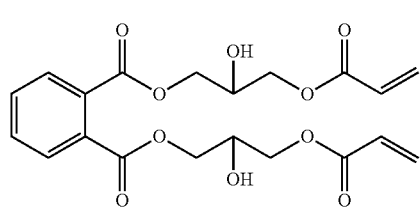
DA-721
(2-105)
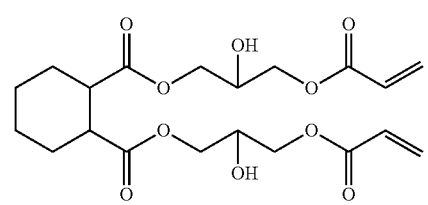
DA-722
(2-106)
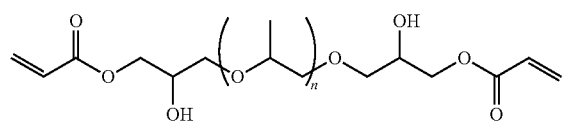
DA-911M
n = 1
(2-107)
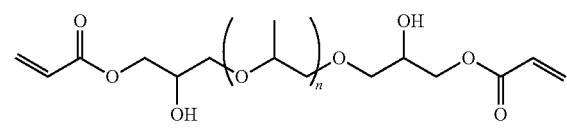
DA-920
n = 3
(2-108)
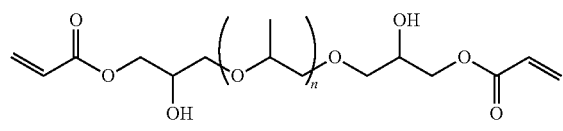
DA-931
n = 11
(2-109)
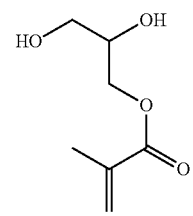

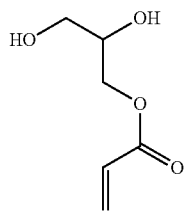 (2-110)

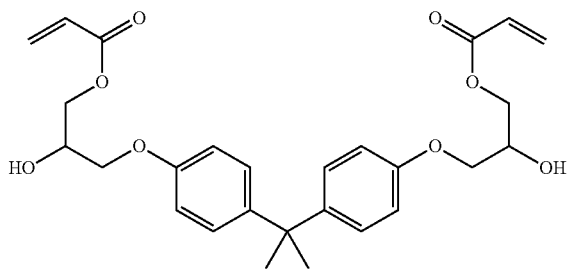 (2-111)

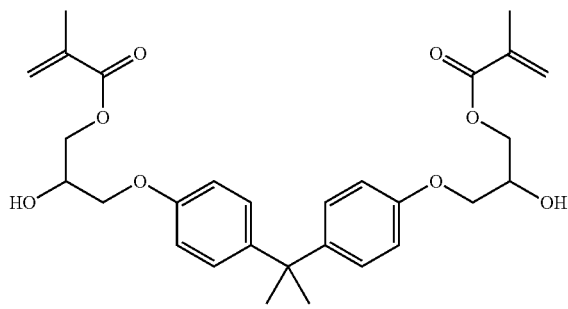 (2-112)

Examples of the Unit-(2)-forming compound include, in addition to the above-described compounds, polybutadienediol (hereafter, also referred to as "PBD"), polyisoprenediol (hereafter, also referred to as "PIP"), and polyolefindiol.

As such polymer diols serving as the Unit-(2)-forming compounds, commercially available products may also be used.

For the commercially available products of the polymer diols, reference can be made to Examples described later.

For the commercially available products of the polymer diols, reference may also be made to Paragraph 0111 in WO2016/152254A.

From the viewpoint of further improving the optical density and the washing resistance of the printed textile, the total content of Unit (1) and Unit (2) in the polymer P relative to the total amount of the polymer P is preferably 50 mass % or more, more preferably 60 mass % or more, still more preferably 80 mass % or more.

In the polymer P, the molar ratio of Unit (2) to Unit (1) (hereafter, also referred to as "molar ratio [Unit (2)/Unit (1)]") is preferably 0.20 or more and less than 1.00, more preferably 0.30 or more and 0.90 or less, still more preferably 0.50 or more and 0.90 or less.

Structural Unit Having Hydrophilic Group

The polymer P preferably includes at least one species of a structural unit having a hydrophilic group.

Specific examples and preferred forms of the hydrophilic group are the same as those described above.

The structural unit having a hydrophilic group is preferably formed from, as a raw material, a hydrophilic-group-introducing compound described later.

The structural unit having a hydrophilic group is particularly preferably a structural unit having an anionic group, specifically, a structural unit represented by the following Formula (3) (hereafter, also referred to as "Unit (3)").

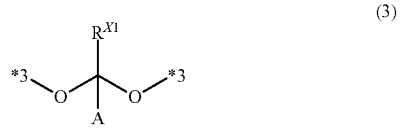 (3)

In Formula (3), $R^{X1}$ represents a hydrogen atom or an alkyl group having 1 to 10 carbon atoms; A represents an anionic group; and two *3's each represent a bonding site.

Unit (3) is preferably bonded to at least Unit (1).

Examples of the anionic group represented by A are the same as the above-described examples of the anionic group.

The anionic group represented by A is preferably a carboxy group or a salt of a carboxy group.

The polymer P may include a form of Unit (3) in which A is a carboxy group and a form of Unit (3) in which A is a salt of a carboxy group.

Relative to the total amount of the polymer P, the content of the structural unit having a hydrophilic group (for example, Unit (3)) is preferably 3 mass % to 30 mass %, more preferably 5 mass % to 20 mass %.

Relative to the total amount of the polymer P, the content of the structural unit having an anionic group may be adjusted in consideration of the acid value (mmol/g) of the polymer P.

Hydrophilic-Group-Introducing Compound

The hydrophilic group can be introduced into the polymer P by using a hydrophilic-group-introducing compound.

Of such hydrophilic-group-introducing compounds, examples of an anionic-group-introducing compound include, a compound in which, in Unit (3), hydrogen atoms are individually bonded to two *3's; and amino acids such as α-amino acids (specifically, lysine, alanine, arginine, asparagine, aspartic acid, cysteine, glutamine, glutamic acid, glycine, histidine, isoleucine, leucine, methionine, phenylalanine, proline, serine, threonine, tryptophan, tyrosine, and valine).

Examples of the compound in which, in Unit (3), hydrogen atoms are individually bonded to two *3's include 2,2-dimethylolpropionic acid (DMPA) and 2,2-dimethylolbutanoic acid (DMBA).

The anionic-group-introducing compound may be treated with, for example, an inorganic base such as sodium hydroxide or potassium hydroxide or an organic base such as triethylamine such that the anionic groups are at least partially neutralized, and used.

The anionic groups may be neutralized during the forming process of the polymer P (for example, the forming process of coloring resin particles) (refer to Examples described later).

Of the hydrophilic-group-introducing compounds, a non-ionic-group-introducing compound is preferably a compound having a polyether structure, more preferably a compound having a polyoxyalkylene group.

The polymer P may include, in addition to the above-described structural units, another structural unit.

However, when the polymer P includes the structural unit having a hydrophilic group, from the viewpoint of the optical density and the washing resistance of the printed textile, and the dispersion stability of the coloring resin particles, the total content of Unit (1), Unit (2), and the structural unit having a hydrophilic group relative to the total amount of the polymer P is preferably 80 mass % or more.

Preferred Form of Polymer P

The polymer P preferably includes the structure of a reaction product of
  the Unit-(1)-forming compound (preferably a diisocyanate compound having a structure in which, in Unit (1), two moieties "—NH(C=O)-*1" are each replaced by an isocyanate group (—NCO group)),
  the Unit-(2)-forming compound (preferably, a compound having a structure in which, in Unit (2), "*2-$Y^1$—" and "—$Y^2$-*2" are each replaced by a hydroxy group, a thiol group, or an amino group), and
  the hydrophilic-group-introducing compound (preferably, a compound in which, in Unit (3), hydrogen atoms are individually bonded to two *3's).

The polymer P preferably includes a urethane bond. Examples of the urethane bond include a urethane bond formed by bonding together Unit (1) and a form of Unit (2) in which $Y^1$ and $Y^2$ are each —O—, and a urethane bond formed by bonding together Unit (1) and Unit (3).

The structure of a terminal of the main chain of the polymer P is not particularly limited; a terminal group of the main chain of the polymer P is preferably an alkyl group having 1 to 20 (more preferably 1 to 10, still more preferably 1 to 6) carbon atoms.

The terminal alkyl group having 1 to 20 (more preferably 1 to 10, still more preferably 1 to 6) carbon atoms can be formed by, for example, using, as a terminal capping agent, an alcohol having 1 to 20 (more preferably 1 to 10, still more preferably 1 to 6) carbon atoms, a thioalcohol having 1 to 20 (more preferably 1 to 10, still more preferably 1 to 6) carbon atoms, or a monoalkylamine having 1 to 20 (more preferably 1 to 10, still more preferably 1 to 6) carbon atoms.

The polymer P is, from the viewpoint of further improving the optical density and the washing resistance of the printed textile, preferably a chain polymer.

The term "chain polymer" means a polymer not including a cross-linked structure.

The chain polymer may include a ring structure. It is appreciated that the chain polymer may include a branched structure.

In the coloring resin particles, the polymer P content is, from the viewpoint of further improving the optical density and the washing resistance of the printed textile, relative to the solid content amount of the coloring resin particles, preferably 10 mass % or more, more preferably 20 mass % or more, still more preferably 30 mass % or more.

In the coloring resin particles, the polymer P content is, from the viewpoint of further improving the optical density of the printed textile, relative to the solid content amount of the coloring resin particles, preferably 90 mass % or less, more preferably 80 mass % or less, still more preferably 70 mass % or less, still more preferably 60 mass % or less.

In the present disclosure, the term "the solid content amount of the coloring resin particles" means, in a case where the coloring resin particles include a solvent (for example, an oil organic solvent described later. The same applies to solvents below), the total amount except for the solvent, or means, in a case where the coloring resin particles do not include a solvent, the total amount of the coloring resin particles.

In the present disclosure, the term "the solid content of the coloring resin particles" means, in a case where the coloring resin particles include a solvent, all the components except for the solvent, or means, in a case where the coloring resin particles do not include a solvent, all the components of the coloring resin particles.

A preferred example of the method for synthesizing the polymer P is an example of causing a reaction of, in the presence of an oil organic solvent described later, the Unit-(1)-forming compound, the Unit-(2)-forming compound, and the hydrophilic-group-introducing compound.

This example of the synthesis method may be performed to synthesize a polymer having a form in which anionic groups serving as hydrophilic groups are not neutralized; this polymer may be used as one of the raw materials to prepare the coloring resin particle dispersion; in the preparation stage, anionic groups of the polymer may be neutralized, to form the polymer P.

The coloring resin particle dispersion obtained above can be directly used as the specified ink; however, the specified ink is preferably prepared by adding, to the coloring resin particle dispersion, another component other than the coloring resin particles.

Oil-Soluble Dye

The coloring resin particles contain at least one oil-soluble dye.

In the oil-soluble dye, "oil-soluble" means a property of having a solubility of 5 mass % or more in methyl ethyl ketone at 20° C.

The oil-soluble dye preferably has a solubility of 1 mass % or less in water at 20° C.

As the oil-soluble dye, in Colour Index (C.I.) Numbers, oil-soluble dyes described with the term "Solvent" are usable.

Specific examples of the oil-soluble dyes include
  C.I. Solvent Yellow 2, 14, 16, 21, 33, 43, 44, 56, 82, 85, 93, 98, 114, 131, 135, 157, 160, 163, 167, 176, 179, 185, 189;
  C.I. Solvent Red 8, 23 24, 25, 49, 52, 109, 111, 119, 122, 124, 135, 146, 149, 150, 168, 169, 172, 179, 195, 196, 197, 207, 222, 227, 312, 313;
  C.I. Solvent Blue 3, 4, 5, 35, 36, 38, 44, 45, 59, 63, 67, 68, 70, 78, 83, 97, 101, 102, 104, 105, 111, 122;
  C.I. Solvent Orange 3, 14, 54, 60, 62, 63, 67, 86, 107;

C.I. Solvent Violet 8, 9, 11, 13, 14, 26, 28, 31, 36, 59;
C.I. Solvent Green 3, 5, 7, 28;
C.I. Solvent Brown 53; and
C.I. Solvent Black 3, 5, 7, 27, 28, 29, 34.

As the oil-soluble dye, an oil-soluble dye obtained by making a reactive dye or an acid dye be oil-soluble is also usable.

The reactive dye having been made to be oil-soluble is, for example, an oil-soluble dye provided by modifying a reactive dye with an alkyl group having 4 or more carbon atoms (for example, RB5A in EXAMPLES described later). The reactive dye employed for being made to be oil-soluble is, for example, C.I. Reactive Black 5.

The acid dye having been made to be oil-soluble is, for example, an oil-soluble dye in which the cation in an acid dye has been subjected to exchange of the counter cations and replaced by a cation having 8 or more carbon atoms.

The acid dye employed for being made to be oil-soluble is, for example, C.I. Acid Black 1.

The oil-soluble dye, from the viewpoint of the optical density of the printed textile, preferably includes an azo dye, more preferably includes an azo dye having an ionic group.

An azo dye not including an ionic group is, for example, C.I. Solvent Black 3.

The azo dye including an ionic group is, for example, C.I. Solvent Black 28.

The azo dye having an ionic group is also, for example, an oil-soluble dye provided by making, be oil-soluble, a reactive dye (for example, C.I. Reactive Black 5) or an acid dye (for example, C.I. Acid Black 1).

In the coloring resin particles, the oil-soluble dye content is, from the viewpoint of further improving the optical density of the printed textile, relative to the solid content amount of the coloring resin particles, preferably 10 mass % or more, more preferably 20 mass % or more, still more preferably 30 mass % or more, still more preferably 40 mass % or more.

In the coloring resin particles, the oil-soluble dye content is, from the viewpoint of further improving the optical density and the washing resistance of the printed textile, relative to the solid content amount of the coloring resin particles, preferably 90 mass % or less, more preferably 80 mass % or less, still more preferably 70 mass % or less.

The ratio of the mass content of the polymer P to the mass content of the oil-soluble dye (hereafter, also referred to as "mass content ratio [P/dye]") is, from the viewpoint of further improving the optical density of the printed textile, preferably 0.10 to 4.00, more preferably 0.10 to 2.50, still more preferably 0.20 to 2.50, still more preferably 0.20 to 1.50, still more preferably 0.25 to 1.00.

Other Component

The coloring resin particles may or may not contain, as needed, in addition to the polymer P and the oil-soluble dye, another component.

From the viewpoint of further improving the optical density and the washing resistance of the printed textile, in the coloring resin particles, the total content of the polymer P and the oil-soluble dye relative to the solid content amount of the coloring resin particles is preferably 80 mass % or more.

From the viewpoint of further improving the optical density and the washing resistance of the printed textile, the solid content amount of the coloring resin particles relative to the total amount of the coloring resin particles is preferably 80 mass % or more.

The other component that can be contained in the coloring resin particles may be an oil organic solvent.

When the coloring resin particles contain an oil organic solvent, they may contain a single oil organic solvent alone or two or more oil organic solvents.

The term "oil organic solvent" means an organic solvent that has a solubility of 10 mass % or less in water at 20° C.

The solubility of the oil organic solvent in water at 20° C. is preferably 5 mass % or less, more preferably 1 mass % or less. When the solubility of the oil organic solvent in water at 20° C. is 5 mass % or less, the oil (organic component) and water become less miscible during emulsification, to further improve the synthesis suitability and the stability of the coloring resin particles.

The oil organic solvent may include an oil organic solvent having volatility or an oil organic solvent having nonvolatility. Of these, the oil organic solvent having nonvolatility has a higher probability of being present in the coloring resin particles.

The term "oil organic solvent having volatility" means an oil organic solvent that has a boiling point of less than 100° C. Examples of the oil organic solvent having volatility include ester-based solvents such as ethyl acetate and ketone-based solvents such as methyl ethyl ketone.

The term "organic solvent having nonvolatility" means an oil organic solvent that has a boiling point of more than 100° C.

The oil organic solvent having nonvolatility is, from the viewpoint of exhibiting nonvolatility during the reaction and from the viewpoint of the dispersion stability during storage of the coloring resin particle dispersion or the ink, preferably an oil organic solvent having a boiling point of 180° C. or more.

Note that, in the present disclosure, the boiling point is the value of a boiling point under standard conditions (1 atm, 25° C.). 1 atm is 101.325 kPa.

Specific examples of the oil organic solvent having nonvolatility include non-halogen phosphoric acid esters (for example, TCP manufactured by DAIHACHI CHEMICAL INDUSTRY CO., LTD.), alkyl group-substituted aromatic compounds (for example, alkene KS-41 manufactured by JXTG Energy Corporation, and KMC500 manufactured by Kureha Chemical Industry Co., Ltd.), long-chain alkyl group-substituted ester compounds (for example, methyl laurate KS-33 manufactured by NOF CORPORATION, and glycerol tris(2-ethylhexanoate) manufactured by FUJIFILM Wako Pure Chemical Corporation), dibasic acid esters (for example, DBE manufactured by INVISTA, dimethyl succinate, dimethyl glutarate, and diisopropyl succinate manufactured by Tokyo Chemical Industry Co., Ltd.), and alkylene glycol derivatives (for example, manufactured by Tokyo Chemical Industry Co., Ltd., ethylene glycol monobutyl ether acetate, diethylene glycol monobutyl ether acetate, diethylene glycol dibutyl ether, and diethylene glycol dibenzoate).

From the viewpoint of the solubility of the dye represented by Formula (M-A), the oil organic solvent is particularly preferably DBE, dimethyl succinate, dimethyl glutarate, diisopropyl succinate, glycerol tris(2-ethylhexanoate), diethylene glycol monobutyl ether acetate, or diethylene glycol dibutyl ether.

When the coloring resin particles include the oil organic solvent, the oil organic solvent content relative to the solid content amount of the coloring resin particles is preferably 0.1 mass % to 20 mass %, more preferably 1 mass % to 15 mass %, still more preferably 3 mass % to 10 mass %.

Volume-Average Particle Size

The coloring resin particles preferably have a volume-average particle size of 200 nm or less, more preferably 20 nm to 200 nm, still more preferably 40 nm to 150 nm. When the coloring resin particles have a volume-average particle size of 200 nm or less, the resultant ink jet ink has even higher ejection performance.

The term "volume-average particle size of the coloring resin particles" means a value measured using a particle size distribution analyzer (for example, Nanotrac UPA EX150, manufactured by NIKKISO CO., LTD., trade name).

In the specified ink, the solid content amount of the coloring resin particles relative to the total amount of the specified ink is preferably 1 to 20 mass %, more preferably 1 to 15 mass %, still more preferably 3 to 10 mass %.

Coloring Resin Particle Dispersion

As the specified ink, a coloring resin particle dispersion containing the coloring resin particles and water may be directly used, or an ink prepared by adding, to a coloring resin particle dispersion containing the coloring resin particles and water, another component may be used.

The coloring resin particle dispersion used herein contains water and the above-described coloring resin particles.

The coloring resin particle dispersion may or may not contain, in addition to water and the coloring resin particles, another component.

From the viewpoint of further improving the optical density and the washing resistance of the printed textile, in the coloring resin particle dispersion, the total content of water and the coloring resin particles relative to the total amount of the coloring resin particle dispersion is preferably 80 mass % or more.

Example of Method for Producing Coloring Resin Particle Dispersion

The production method for producing the coloring resin particle dispersion is not particularly limited.

Hereinafter, an example of the method for producing the coloring resin particle dispersion (hereafter, also referred to as "production method A") will be described.

The production method A includes,
a step of preparing an oil-phase component including an oil organic solvent (specifically, an oil organic solvent having volatility and/or an oil organic solvent having nonvolatility), the polymer P or the polymer P in which anionic groups serving as hydrophilic groups are to be neutralized, and an oil-soluble dye,
a step of preparing an aqueous-phase component including water (and a neutralizer as needed), and
an emulsification step of mixing together the oil-phase component and the aqueous-phase component, and emulsifying the resultant mixture to obtain an emulsion.

In the production method A, the emulsification step is performed to form the coloring resin particles and to disperse the formed coloring resin particles in water, to thereby provide a coloring resin particle dispersion in which the coloring resin particles are dispersed in water.

In the case of using, as the oil-phase component, an oil-phase component including the polymer P in which anionic groups serving as hydrophilic groups are to be neutralized and using, as the aqueous-phase component, an aqueous-phase component including water and a neutralizer, in the emulsification step, in the polymer P in which anionic groups are to be neutralized, anionic groups are at least partially neutralized, to thereby form coloring resin particles containing the polymer P including neutralized anionic groups (for example, —COONa).

As the neutralizer, a basic compound such as sodium hydroxide, potassium hydroxide, or triethylamine is usable.

In the emulsification step, the process of performing emulsification is not particularly limited, but may be, for example, emulsification using an emulsification apparatus such as a homogenizer (for example, a dispersing machine).

In the emulsification, the number of revolutions of the dispersing machine is, for example, 5000 rpm to 20000 rpm, preferably 10000 rpm to 15000 rpm. This term "rpm" is the abbreviation of revolutions per minute.

In the emulsification, the time for revolutions is, for example, 1 minute to 120 minutes, preferably 3 minutes to 60 minutes, more preferably 3 minutes to 30 minutes, still more preferably 5 minutes to 15 minutes.

In the emulsification step, emulsification may be performed under heating.

Such emulsification under heating enables more efficient formation of the coloring resin particles.

In addition, the emulsification under heating facilitates removal of at least partially the oil organic solvent in the oil-phase component from the mixture.

In the case of performing emulsification under heating, the heating temperature is preferably 35° C. to 70° C., more preferably 40° C. to 60° C.

The production method A may include a heating step of heating the emulsion or a mixture of the emulsion and water to remove at least partially the oil organic solvent.

In the heating step, the heating temperature is preferably 35° C. to 70° C., more preferably 40° C. to 60° C.

Aqueous Organic Solvent

The specified ink preferably contains at least one aqueous organic solvent.

In this case, the ink has high stability (specifically, for example, sedimentation is less likely to occur) and also has high ejection performance through the ink jet head.

Preferred examples of the aqueous organic solvent that can be contained in the specified ink are the same as the above-described preferred examples of the aqueous organic solvent that can be contained in the pretreatment liquid according to the present disclosure.

In the specified ink, the aqueous organic solvent content relative to the total amount of the specified ink is preferably 5 mass % to 50 mass %, more preferably 5 mass % to 40 mass %, still more preferably 10 mass % to 30 mass %.

When the aqueous organic solvent content is within such a range, the specified ink has high stability (for example, sedimentation is less likely to occur) and also has, as an ink jet ink, high ejection performance.

Cross-Linking Agent

The specified ink may further include at least one cross-linking agent.

The cross-linking agent is preferably a compound that has at least two cross-linking groups.

The cross-linking agent has a cross-linking group that is preferably, for example, a carboxy group, a hydroxyl group, a sulfonic group, or an amide group.

Examples of the cross-linking agent include blocked isocyanate-based compounds, oxazoline-based compounds, and carbodiimide compounds.

In particular, preferred are blocked isocyanate-based compounds provided by blocking, using a blocking agent, TMP (trimethylolpropane) adducts or isocyanurates of diisocyanates (for example, HDI (hexamethylene diisocyanate), H6XDI (hydrogenated xylylene diisocyanate), IPDI (isophorone diisocyanate), and H12MDI (dicyclohexylmethane diisocyanate)); and carbodiimide compounds.

For the blocked isocyanate-based compounds, the blocking agent is, from the viewpoint of unblocking temperature, preferably DEM (diethyl malonate), DIPA (diisopropylamine), TRIA (1,2,4-triazole), DMP (3,5-dimethylpyrazole), or MEKO (butanone oxime).

Such a blocked isocyanate-based compound can also be used as an oligomer provided by causing partially the isocyanate groups to react with polyol, polycarbonate, polyester, or polyether, for example.

As the carbodiimide compounds, preferred are CARBODILITE cross-linking agents for aqueous resins, E-02, E-03A, and E-05 (all are product names) manufactured by Nisshinbo Chemical Inc.; and, from the viewpoint of preservation stability and reactivity, particularly preferred is E-05.

As the unblocking temperature of the cross-linking agent, from the viewpoint of cross-linking efficiency, the lower the unblocking temperature, the more preferable it is; however, from the viewpoint of preservation stability, the higher the unblocking temperature, the more preferable it is.

From the viewpoint of the balance between these, the unblocking temperature is preferably 90° C. to 180° C., more preferably 90° C. to 120° C., particularly preferably 110° C. to 120° C.

The cross-linking agent is preferably prepared to have a hydrophilic group, and added, as the resultant water-soluble or self-emulsifiable agent, to the ink. In this state, the ink provided by the addition has a viscosity that is a low viscosity and has high re-dispersibility.

The cross-linking agent may be cross-linking agent particles.

The cross-linking agent particles preferably have an average particle size of, from the viewpoint of improving the ink jet ejection performance, 200 nm or less.

The term "average particle size" used herein can be the value of a volume-average particle size (MV) measured using a particle size distribution analyzer (Nanotrac UPA EX150, manufactured by NIKKISO CO., LTD., trade name).

The cross-linking agent particles are not particularly limited, and examples include ELASTRON BN-77 (blocked isocyanate, particle size: 19 nm, unblocking temperature: 120° C. or more, manufactured by DAI-ICHI KOGYO SEIYAKU CO., LTD.), ELASTRON BN-27 (blocked isocyanate, particle size: 108 nm, unblocking temperature: 180° C. or more, manufactured by DAI-ICHI KOGYO SEIYAKU CO., LTD.), Duranate WM44-70G (blocked isocyanate, particle size: 42 nm, unblocking temperature: about 90° C., manufactured by Asahi Kasei Corporation), and TRIXENE AQUA BI200 (blocked isocyanate, particle size: 94 nm, unblocking temperature: 110-120° C., manufactured by BAXENDEN Chemicals Ltd.).

When the specified ink contains a cross-linking agent, in the specified ink, the cross-linking agent content relative to the total amount of the specified ink is preferably 0.1 mass % to 10 mass %, more preferably 0.5 mass % to 8 mass %, still more preferably 1 mass % to 5 mass %.

Pigment

The specified ink may further include, from the viewpoint of adjusting the hue or improving the color density, at least one pigment.

Examples of the pigment include
carbon black, aniline black;
C.I. Pigment Yellow 3, 12, 53, 55, 74, 81, 83, 93, 94, 95, 97, 98, 100, 101, 104, 108, 109, 110, 117, 120, 128, 138, 153, 155, 180, 185;
C.I. Pigment Red 112, 114, 122, 123, 146, 149, 166, 168, 170, 172, 177, 178, 179, 185, 190, 193, 202, 206, 209, 219;
C.I. Pigment Violet 19, 23;
C.I. Pigment Orange 36, 43, 64;
C.I. Pigment Blue 15, 15:1, 15:2, 15:3, 15:4, 15:6, 16, 17:1, 56, 60, 63; and
C.I. Pigment Green 36.

When the specified ink includes the pigment, in the specified ink, the pigment content relative to the total amount of the specified ink is preferably 0.5 mass % to 10 mass %, more preferably 0.5 mass % to 8 mass %, still more preferably 0.5 mass % to 5 mass %.

In the preparation of the specified ink, an aqueous dispersion of the pigment prepared by using a dispersing agent to disperse the pigment in water (hereafter, also referred to as "aqueous pigment dispersion") is also usable. As the aqueous pigment dispersion, for example, a pigment dispersion described in JP2012-7148A is usable. As the aqueous pigment dispersion, commercially available products such as Pro-jet Black APD1000 (manufactured by Fujifilm Imaging Colorants Inc.) are also usable.

As the pigment, self-dispersible pigments are also usable.

Such a self-dispersible pigment is a pigment that is dispersible in water without using a dispersing agent. The self-dispersible pigment is, for example, a pigment in which, to its surfaces, at least one species selected from the group consisting of hydrophilic groups such as a carbonyl group, a hydroxyl group, a carboxyl group, a sulfo group, and a phosphoric acid group and salts of the foregoing is introduced directly or using a chemical bond to another group on the surfaces.

The self-dispersible pigment is preferably self-dispersible carbon black.

Examples of the self-dispersible pigment usable include commercially available products such as self-dispersible carbon black CAB-O-JET series 200, 300, and 400 (all are manufactured by Cabot Corporation), BONJET series CW-1 (carboxy group: 500 µmol/g), CW-2 (carboxy group: 470 µmol/g) (all are manufactured by ORIENT CHEMICAL INDUSTRIES CO., LTD.), and Aqua-Black 162 (carboxyl group: about 800 µmol/g) from TOKAI CARBON CO., LTD.

As the pigment, an aqueous dispersion of a pigment prepared by using a dispersing agent to disperse the pigment in water or a self-dispersible pigment is preferably usable.

Wax

The specified ink may contain at least one wax.

This further improves the washing resistance of the printed textile.

The wax is preferably present in the form of particles in the specified ink.

Hereafter, the wax in the form of particles will be referred to as "wax particles".

As the wax particles, a dispersion in which the wax is dispersed in water is preferably used.

The wax is preferably polyethylene wax, paraffin wax, or carnauba wax.

The melting point of the wax is, from the viewpoint of improving the stability and the frictional properties, preferably in the range of 60° C. to 120° C., more preferably in the range of 60° C. to 100° C. An increase in the melting point improves the stability of the textile printing ink; however, not excessively increasing the melting point is effective for improving the frictional properties.

The melting point of the wax can be measured using an ordinary melting point measurement apparatus.

The volume-average particle size (Mw) of the wax particles is, from the viewpoint of the ink jet ejection performance, preferably 0.3 μm or less, more preferably 0.2 μm or less, particularly preferably 0.1 μm or less.

The volume-average particle size can be measured by the same method as in the above-described coloring resin particles.

When the specified ink includes wax, the wax content relative to the total amount of the specified ink is preferably 0.1 mass % to 10 mass %, more preferably 0.5 mass % to 8 mass %, still more preferably 1 mass % to 5 mass %.

As the wax particles, commercially available products may be used.

Examples of the commercially available products include Polyron L-787 (manufactured by Chukyo Yushi Co., Ltd., polyethylene, nonionic, melting point: 102° C., volume-average particle size: 0.1 μm), Hidorin-703 (manufactured by Chukyo Yushi Co., Ltd., paraffin, anionic, melting point: 75° C., volume-average particle size: 0.1 μm), R108 (manufactured by Chukyo Yushi Co., Ltd., paraffin, nonionic, melting point: 66° C., volume-average particle size: 0.2 μm), and Selosol 524 (manufactured by Chukyo Yushi Co., Ltd., carnauba, nonionic, melting point: 83° C., volume-average particle size: 0.07 μm).

Surfactant

The specified ink can contain at least one surfactant.

The surfactant is not particularly limited, and publicly known surfactants such as anionic surfactants, cationic surfactants, and nonionic surfactants are usable.

The surfactant is, from the viewpoint of the ejection performance in the case of providing an ink jet ink, preferably nonionic surfactants, of these, particularly preferably acetylene-based surfactants.

Examples of commercially available products of the acetylene-based surfactants include SURFYNOL (registered trademark) series manufactured by Nissin Chemical Industry Co., Ltd., and OLFINE (registered trademark) series manufactured by Nissin Chemical Industry Co., Ltd.

When the specified ink contains a surfactant, the surfactant content is, from the viewpoint of the ejection performance in the case of providing an ink jet ink, relative to the total amount of the ink, preferably 0.1 mass % to 2.0 mass %, more preferably 0.5 mass % to 2.0 mass %.

Other Component

The specified ink may contain, in addition to the above-described components, another component.

Examples of the other component include a dye other than the above-described oil-soluble dyes, a pH adjusting agent, a fluorescent brightening agent, a surface tension modifier, an anti-foaming agent, an anti-drying agent, a lubricant, a thickener, an ultraviolet absorbent, an anti-fading agent, an antistatic agent, a matting agent, an antioxidant, a resistivity control agent, an anticorrosive, a reduction inhibitor, a preservative, a fungicide, and a chelating agent.

For the other component, reference may be made to descriptions in WO2017/131107A.

The specified ink preferably has a surface tension of 20 mN/m to 70 mN/m, more preferably 25 mN/m to 60 mN/m.

The term "surface tension" used herein means a value measured at 25° C.

The surface tension can be measured by using, for example, an Automatic Surface Tentiometer CBVP-Z (manufactured by Kyowa Interface Science Co., Ltd.).

The specified ink preferably has a viscosity of 40 mPa·s or less, more preferably 30 mPa·s or less.

The term "viscosity" used herein is a value measured at 25° C.

As the viscometer, for example, a VISCOMETER TV-22 viscometer (manufactured by Toki Sangyo Co., Ltd.) is usable.

Ink Jet Textile Printing Method

Hereinafter, as a preferred example of the textile printing method using the pretreatment liquid according to the present disclosure and the ink set according to the present disclosure, an ink jet textile printing method will be described in terms of an example thereof (hereafter, also referred to as "ink jet textile printing method A").

However, as described above, the textile printing method using the pretreatment liquid according to the present disclosure and the ink set according to the present disclosure is not necessarily limited to the ink jet textile printing method.

The ink jet textile printing method A uses the above-described ink set according to the present disclosure (specifically, an ink set including the pretreatment liquid according to the present disclosure and the specified ink), and the ink jet textile printing method A has a step of pretreating a textile by applying the pretreatment liquid according to the present disclosure (hereafter, also referred to as "pretreatment step"), a step of applying the specified ink by an ink jet process to the pretreated textile (hereafter, also referred to as "ink application step"), and a step of heat-treating the textile to which the specified ink has been applied, to obtain a printed textile (hereafter, also referred to as "heat treatment step").

The ink jet textile printing method A may have, as needed, another step.

In the ink jet textile printing method A, the above-described ink set according to the present disclosure is used, to thereby provide a printed textile that has high optical density, high washing resistance, and good texture.

In the ink jet textile printing method A, steps that can be included in the ordinary textile printing method such as the transfer step and the textile printing paste application step are not necessary.

In addition, in the ink jet textile printing method A, the steam treatment step (specifically, the step of performing a steam treatment to fix the image), which can be performed in the ordinary ink jet textile printing method, is also not necessary. In the ordinary ink jet textile printing method, in particular, the steam treatment step is performed to ensure the optical density and the washing resistance of the printed textile in some cases.

In the ink jet textile printing method A, even when the steam treatment step is omitted, an image having high optical density and high washing resistance can be formed on a textile.

Textile

The ink jet textile printing method A is applicable to various types of textiles.

Examples of the types of fibers in the textiles include synthetic fibers such as nylon, polyester, and acrylonitrile; semi-synthetic fibers such as acetate and rayon; natural fibers such as cotton, silk, and fur; and mixed fibers composed of two or more selected from the group consisting of synthetic fibers, semi-synthetic fibers, and natural fibers.

The type of the fiber in such a textile is preferably at least one selected from the group consisting of cotton and polyester.

Examples of the form of the textile include woven fabrics, knitted fabrics, and nonwoven fabrics.

The textile may be a textile for a textile product.

Examples of the textile product include clothing items (for example, T-shirts, sweatshirts, jerseys, pants, sweat suits, one-piece dresses, and blouses), bedclothes, and handkerchiefs.

Pretreatment Step

The pretreatment step is a step of pretreating a textile by applying the pretreatment liquid according to the present disclosure.

The process of applying the pretreatment liquid to the textile is not particularly limited, and examples include a coating process, a padding process, an ink jet process, a spraying process, and a screen printing process.

Ink Application Step

The ink application step is a step of applying, to the pretreated textile, the specified ink by an ink jet process.

In the present disclosure, textiles to which the ink has been applied may be referred to as colored textiles.

The application of the specified ink by the ink jet process can be performed using a publicly known ink jet formation apparatus.

The ink jet formation apparatus is not particularly limited, and a publicly known ink jet formation apparatus that can achieve the target resolution can be appropriately selected and used.

The ink jet formation apparatus is, for example, an apparatus including an ink supply system, a temperature sensor, and heating means.

The ink supply system includes, for example, a source tank including the specified ink, supply pipes, an ink supply tank disposed immediately upstream of an ink jet head, a filter, and a piezoelectric ink jet head. The piezoelectric ink jet head can be driven to eject multi-size dots of, preferably 1 pL (picoliter) to 100 pL, more preferably 8 pL to 30 pL, at a resolution of, preferably 320 dpi×320 dpi to 4000 dpi×4000 dpi, more preferably 400 dpi×400 dpi to 1600 dpi×1600 dpi, still more preferably 720 dpi×720 dpi. Note that the term "dpi (dot per inch)" means the number of dots per 2.54 cm (1 inch).

Heat Treatment Step

The heat treatment step is a step of heat-treating the textile to which the specified ink has been applied, to obtain a printed textile.

In this step, the heat treatment inferentially causes the following: the coloring resin particles in the specified ink are separated from each other; in the surface layer region of the textile, the action of the specified onium salt compound aggregates the oil-soluble dye, and the polymer P forms a polymer film including the aggregated oil-soluble dye. This inferentially results in, in the surface layer region of the textile, formation of an image having high fixability.

In the heat treatment step, the heat treatment temperature (temperature of the image) is preferably 100° C. to 220° C., more preferably 130° C. to 200° C.

In the heat treatment step, the time for the heat treatment is preferably 20 seconds to 300 seconds, more preferably 30 seconds to 240 seconds, still more preferably 40 seconds to 180 seconds.

In the heat treatment step, the heat treatment may be a steam treatment publicly known in ink jet textile printing, but is, from the viewpoint of simplifying the step, preferably a heat treatment other than the steam treatment.

The heat treatment other than the steam treatment is preferably a heat treatment in the form of heat-pressing the textile to which the ink has been applied (namely, the colored textile). In this form of heat treatment, the colored textile is heat-pressed, to thereby heat-treat the image in the colored textile.

The heat-pressing can be performed using a publicly known heat-press machine.

As described above, in the ink jet textile printing method A, even in the case of omitting the steam treatment, the heat treatment other than the steam treatment can be performed to form, on a textile, an image having high optical density and high washing resistance.

The ink jet textile printing method A may include, in addition to the above-described steps, another step.

Examples of the other step include publicly known steps in the ink jet textile printing method, such as a posttreatment step of posttreating, using a posttreatment agent, the colored textile having been subjected to the heat treatment step.

Printed Textile

The printed textile according to the present disclosure includes a textile and an image.

The image includes the specified onium salt compound (specifically, the onium salt compound represented by Formula (A) or Formula (B)), an oil-soluble dye, and the polymer P including a hydrophilic group.

The printed textile according to the present disclosure may include, as needed, another element.

The printed textile according to the present disclosure has high optical density, high washing resistance, and good texture.

The reasons why such advantages are provided are the same as those described above.

Preferred examples of the textile, the specified onium salt compound, the oil-soluble dye, and the polymer P including a hydrophilic group are also the same as those described above.

The image may include, as needed, in addition to the above-described components, another component. For the component that can be contained in the image, reference can be made to the above-described components in the printed textile according to the present disclosure and the above-described components in the specified ink.

The method for producing the printed textile according to the present disclosure is not particularly limited.

The printed textile according to the present disclosure is preferably produced using the ink set according to the present disclosure.

Specifically, the production is achieved by a method of pretreating a textile by applying the pretreatment liquid according to the present disclosure, applying, to the pretreated textile, the specified ink, and heat-treating the textile to which the specified ink has been applied (preferably, an ink jet textile printing method).

EXAMPLES

Hereinafter, Examples of the present disclosure will be described; however, the present disclosure is not limited to the following Examples.

Preparation of Specified Onium Salt Compounds and Comparative Compounds

As the specified onium salt compounds serving as components in pretreatment liquids, O-1 to O-28 below were prepared; as comparative compounds, OR-1 to OR-3 below were prepared.

For each of the compounds, the molecular weight and C log P (hereafter, simply referred to as "C log P") of the cation structure will also be described below.

In the following "Classification" columns,

"(A1)" means belonging to the onium salt compound represented by Formula (A) and also belonging to the onium salt compound represented by Formula (A1), "(A2)" means belonging to the onium salt compound represented by Formula (A) and also belonging to the onium salt compound represented by Formula (A2), "(A)" means belonging to the onium salt compound represented by Formula (A), but not belonging to the onium salt compound represented by Formula (A1), "(B1)" means belonging to the onium salt compound represented by Formula (B) and also belonging to the onium salt compound represented by Formula (B1), "(B2)" means belonging to the onium salt compound represented by Formula (B) and also belonging to the onium salt compound represented by Formula (B2), and "(B)" means belonging to the onium salt compound represented by Formula (B), but not belonging to the onium salt compound represented by Formula (B1) or the onium salt compound represented by Formula (B2) (The same applies to the "Classification" columns in Table 1-1 and Table 2-1 described later).

| | Specified onium salt compound or comparative compound | | | | |
|---|---|---|---|---|---|
| | Cation | | | | |
| | Cation structure | ClogP | Molecular weight | Counter anion | Classification |
| O-1 | 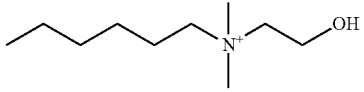 | −1.72 | 174 | Cl⁻ | (A1) |
| O-2 | 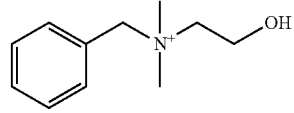 | −2.02 | 180 | Cl⁻ | (A1) |
| O-3 | 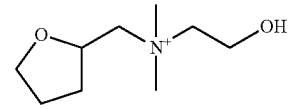 | −2.44 | 174 | Cl⁻ | (A1) |
| O-4 | 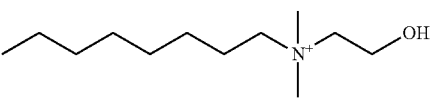 | −0.66 | 202 | Cl⁻ | (A1) |
| O-5 | 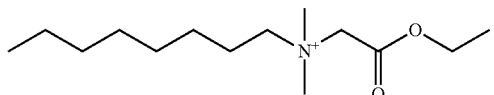 | 0.23 | 244 | Cl⁻ | (A) |
| O-6 | 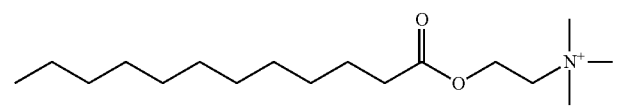 [SMILES: CCCCCCCCCCCC(=O)OCC[N+](C)(C)C] | 1.82 | 287 | Cl⁻ | (A) |
| O-7 | 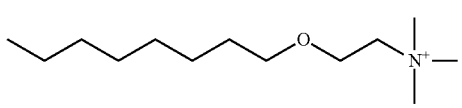 | −0.04 | 216 | Cl⁻ | (A) |
| O-8 | 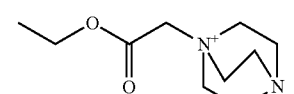 | 0.37 | 199 | Cl⁻ | (A) |
| O-9 | 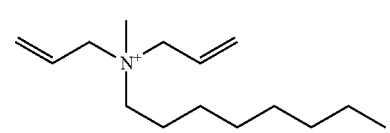 [SMILES: C=CC[N+](C)(CC=C)CCCCCCCC] | −0.01 | 224 | Br⁻ | (A2) |

-continued

| | Specified onium salt compound or comparative compound | | | | |
|---|---|---|---|---|---|
| | Cation | | | | |
| | Cation structure | ClogP | Molecular weight | Counter anion | Classification |
| O-10 | | 5.13 | 307 | Br⁻ | (A) |
| O-11 | | −0.96 | 208 | Cl⁻ | (A1) |
| O-12 | | 1.16 | 264 | Cl⁻ | (A1) |
| O-13 | | 2.32 | 307 | Cl⁻ | (A) |
| O-14 | | 0.05 | 220 | Cl⁻ | (A1) |
| O-15 | | 0.09 | 222 | Cl⁻ | (A1) |
| O-16 | | 0.34 | 248 | Cl⁻ | (A1) |
| O-17 | | 1.80 | 233 | Cl⁻ | (A) |
| O-18 | | 0.19 | 252 | Cl⁻ | (A1) |

-continued
| | Specified onium salt compound or comparative compound | | | | |
|---|---|---|---|---|---|
| | Cation | | | | |
| | Cation structure | ClogP | Molecular weight | Counter anion | Classification |
| O-19 | 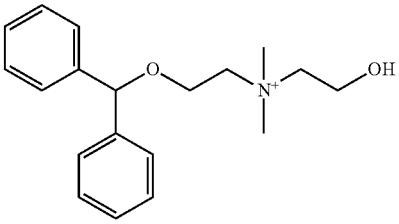 [SMILES: C[N+](C)(CCO)CCOC(c1ccccc1)c1ccccc1] | 0.38 | 300 | Cl⁻ | (A1) |
| O-20 | 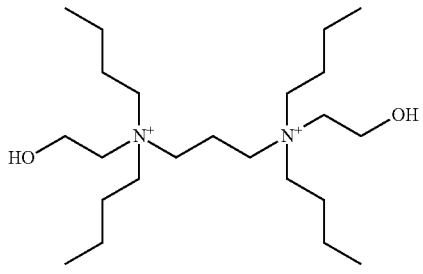 [SMILES: CCCC[N+](CCO)(CCCC)CCC[N+](CCO)(CCCC)CCCC] | 0.42 | 389 | 2Br⁻ | (B1) |
| O-21 | 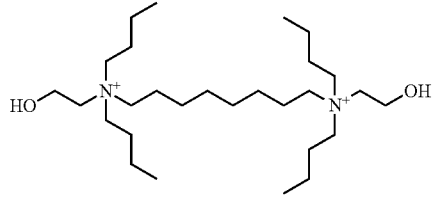 [SMILES: CCCC[N+](CCO)(CCCC)CCCCCCCC[N+](CCO)(CCCC)CCCC] | 0.10 | 459 | 2Br⁻ | (B1) |
| O-22 | 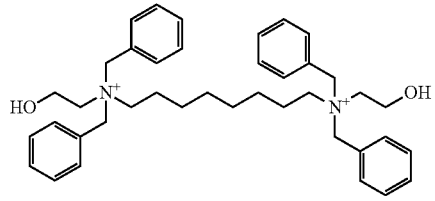 [SMILES: OCC[N+](CCCCCCCC[N+](CCO)(Cc1ccccc1)Cc1ccccc1)(Cc1ccccc1)Cc1ccccc1] | 1.87 | 595 | 2Br⁻ | (B1) |
| O-23 | 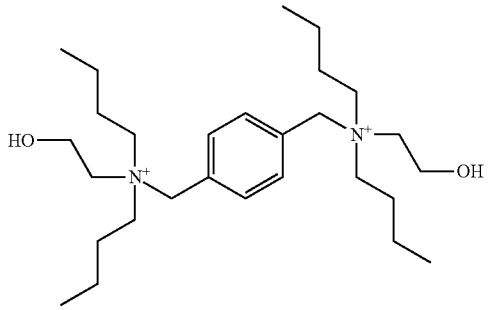 [SMILES: CCCC[N+](CCO)(CCCC)Cc1ccc(C[N+](CCO)(CCCC)CCCC)cc1] | 0.17 | 451 | 2Cl⁻ | (B1) |
| O-24 | 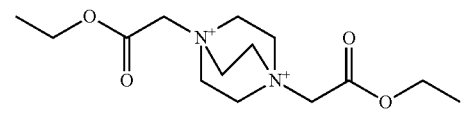 [SMILES: CCOC(=O)C[N+]12CC[N+](CC(=O)OCC)(CC1)CC2] | 0.27 | 286 | 2Cl⁻ | (B2) |
| O-25 | 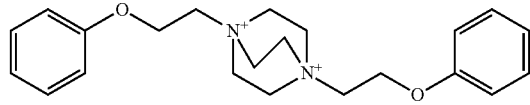 [SMILES: c1ccc(OCC[N+]23CC[N+](CCOc4ccccc4)(CC2)CC3)cc1] | 3.11 | 355 | 2Cl⁻ | (B2) |

-continued

| | Specified onium salt compound or comparative compound | | | | |
|---|---|---|---|---|---|
| | Cation | | | | |
| | Cation structure | ClogP | Molecular weight | Counter anion | Classification |
| O-26 | 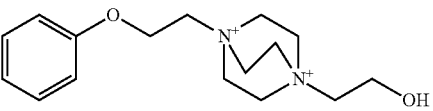 [SMILES: OCC[N+]12CC[N+](CCOc3ccccc3)(CC1)CC2] | 0.53 | 278 | Cl⁻/Br⁻ | (B2) |
| O-27 | 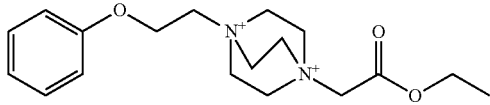 [SMILES: CCOC(=O)C[N+]12CC[N+](CCOc3ccccc3)(CC1)CC2] | 1.69 | 320 | 2Cl⁻ | (B2) |
| O-28 | 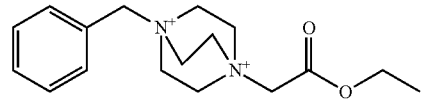 [SMILES: CCOC(=O)C[N+]12CC[N+](Cc3ccccc3)(CC1)CC2] | 0.63 | 290 | 2Cl⁻ | (B2) |
| OR-1 | 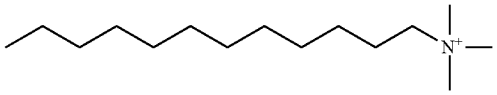 [SMILES: CCCCCCCCCCCC[N+](C)(C)C] | 0.56 | 228 | Cl⁻ | Comparative |
| OR-2 | 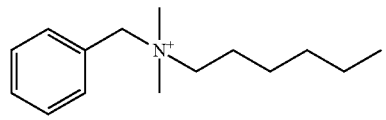 [SMILES: CCCCCC[N+](C)(C)Cc1ccccc1] | 0.01 | 220 | Cl⁻ | Comparative |
| OR-3 | 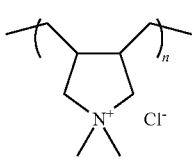 | −1.41 | 8500 | Cl⁻ | Comparative |

Hereinafter, synthesis examples of some of the above-described specific examples will be described. The other specific examples can be synthesized with reference to the following synthesis examples.

Synthesis Example of O-8

In a 1000 mL three-neck recovery flask, to a solution containing 30 g of 1,4-diazabicyclo[2,2,2]octane (manufactured by FUJIFILM Wako Pure Chemical Corporation) and 315.54 g of acetonitrile at 0° C., a solution containing 33.11 g of ethyl chloroacetate (manufactured by FUJIFILM Wako Pure Chemical Corporation) and 78.91 g of acetonitrile was added dropwise. After the dropwise addition, the content was stirred at room temperature for 16 hours, and acetonitrile was driven off under a reduced pressure; to the precipitated solid, 200 g of ethyl acetate was added and the content was stirred for 1 hour and filtered. The resultant filter cake was washed with 200 g of ethyl acetate and subsequently dried to obtain O-8 (yield amount: 61.02 g, yield ratio: 97%). The structure was identified by ¹H-NMR (methanol). The results are as follows.

¹H-NMR (400 MHz, MeOH-d4): 4.36 (s, 2H), 4.33 (q, J=7.1 Hz, 2H), 3.70 (dd, J=7.6, 7.6 Hz, 2H), 3.27 (dd, J=7.6 Hz, 7.6 Hz, 6H), 1.34 (t, J=7.1 Hz, 3H)

Synthesis Example of O-9

In a 100 mL three-neck recovery flask, 7.50 g of diallylmethylamine (manufactured by FUJIFILM Wako Pure Chemical Corporation) and 12.23 g of 1-bromooctane (manufactured by FUJIFILM Wako Pure Chemical Corporation) were stirred at 110° C. for 16 hours and subsequently cooled to 70° C. To this, 60 g of ethyl acetate was added and stirring was performed for 15 minutes. From the resultant mixture, the supernatant (ethyl acetate) was removed and furthermore ethyl acetate was driven off under a reduced pressure to obtain O-9 (yield amount: 16.72 g, yield ratio: 88%). The structure was identified by ¹H-NMR (methanol). The results are as follows.

¹H-NMR (400 MHz, MeOH-d4): 6.23-6.09 (m, 2H), 5.84-5.74 (m, 4H), 4.06 (d, J=7.4 Hz, 4H), 3.35 (t, J=8.1 Hz, 2H), 3.09 (s, 3H), 1.94-1.80 (m, 2H), 1.50-1.32 (m, 10H), 0.95 (t, J=6.8 Hz, 3H)

Synthesis Example of O-12

In a 100 mL three-neck recovery flask, 13.01 g of dibutylaminoethanol (manufactured by FUJIFILM Wako Pure Chemical Corporation) and 9.02 g of benzyl chloride (manufactured by FUJIFILM Wako Pure Chemical Corporation) were stirred at 90° C. for 3 hours; subsequently, to this, 22.03 g of isopropyl alcohol was added and stirring was further performed for 5 hours. From the resultant mixture, isopropyl alcohol was driven off under a reduced pressure; subsequently, to this, at 70° C., 60 g of ethyl acetate was added, stirring was performed for 15 minutes, and subsequently the supernatant was removed. The precipitated solid was collected by filtration and dried, to obtain O-12 (yield amount: 16.43 g, yield ratio: 74%). The structure was identified by $^1$H-NMR (methanol). The results are as follows.

$^1$H-NMR (400 MHz, MeOH-d4): 7.61-7.49 (m, 5H), 4.67 (s, 2H), 4.09-4.02 (m, 2H), 3.41 (t, J=5.1 Hz, 2H), 3.33-3.19 (m, 4H), 1.93-1.79 (m, 4H), 1.47-1.35 (m, 4H), 1.03 (t, J=7.5 Hz, 6H)

Synthesis Example of O-14

In a 100 mL three-neck recovery flask, 11.50 g of piperidineethanol (manufactured by FUJIFILM Wako Pure Chemical Corporation) and 9.02 g of benzyl chloride (manufactured by FUJIFILM Wako Pure Chemical Corporation) were stirred at 90° C. for 2 hours; subsequently, to this, 22.16 g of isopropyl alcohol was added, and stirring was further performed for 6 hours. From the resultant mixture, isopropyl alcohol was driven off under a reduced pressure; to this, at 70° C., 60 g of ethyl acetate was added and stirring was performed for 15 minutes; subsequently, the supernatant was removed. The precipitated solid was collected by filtration and dried, to obtain O-14 (yield amount: 18.96 g, yield ratio: 85%). The structure was identified by $^1$H-NMR (methanol). The results are as follows.

$^1$H-NMR (400 MHz, MeOH-d4): 7.65-7.40 (m, 5H), 4.75 (s, 2H), 4.15-4.08 (m, 2H), 3.59-3.51 (m, 2H), 3.46 (t, J=5.1 Hz, 2H), 3.42-3.33 (m, 2H), 2.05-1.91 (m, 4H), 1.83-1.73 (m, 1H), 1.64-1.54 (m, 1H)

Synthesis Example of O-17

In a 200 mL three-neck recovery flask, 8 g of 1,4-diazabicyclo[2,2,2]octane (manufactured by FUJIFILM Wako Pure Chemical Corporation), 12.8 g of β-chlorophenetole (manufactured by FUJIFILM Wako Pure Chemical Corporation), and 20.80 g of isopropyl alcohol were stirred at 70° C. for 16 hours. From the resultant mixture, isopropyl alcohol was driven off under a reduced pressure; to this, at 70° C., 60 g of ethyl acetate was added and stirring was performed for 15 minutes; subsequently, the supernatant was removed. The precipitated solid was collected by filtration and dried, to obtain O-17 (yield amount: 18.03 g, yield ratio: 95%). The structure was identified by $^1$H-NMR (methanol). The results are as follows.

$^1$H-NMR (400 MHz, MeOH-d4): 7.33-7.26 (m, 2H), 7.02-6.94 (m, 3H), 4.51-4.44 (m, 2H), 3.76-3.71 (m, 2H), 3.52 (dd, J=7.5 Hz, 7.5 Hz, 6H), 3.20 (dd, J=7.5 Hz, 7.5 Hz, 6H)

Synthesis Example of O-21

In a 200 mL three-neck recovery flask, 5 g of 1,8-dibromooctane (manufactured by FUJIFILM Wako Pure Chemical Corporation), 7.30 g of dibutylaminoethanol (manufactured by FUJIFILM Wako Pure Chemical Corporation), and 12.30 g of 2-pyrrolidone were stirred at 110° C. for 10 hours, and subsequently cooled to 70° C.; to this, 160 g of ethyl acetate was added and stirring was performed for 30 minutes. The precipitated viscous substance was isolated by filtration, washed with 40 g of acetonitrile, subsequently collected by filtration, and dried, to obtain O-21 (yield amount: 9.50 g, yield ratio: 84%). The structure was identified by $^1$H-NMR (DMSO). The results are as follows.

$^1$H-NMR (400 MHz, DMSO-d6): 4.24 (s, 2H), 3.97 (t, 4H), 3.43-3.22 (m, 16H), 1.71-1.50 (m, 12H), 1,29-1.24 (m, 12H), 0.89-0.80 (t, 12H)

Synthesis Example of O-25

In a 200 mL three-neck recovery flask, 5 g of 1,4-diazabicyclo[2,2,2]octane (manufactured by FUJIFILM Wako Pure Chemical Corporation), 16 g of β-chlorophenetole (manufactured by FUJIFILM Wako Pure Chemical Corporation), and 20.99 g of 2-pyrrolidone were stirred at 110° C. for 16 hours, and subsequently cooled to 70° C.; to this, 160 g of ethyl acetate was added and stirring was performed for 30 minutes. The precipitated powder was collected by filtration, washed with 40 g of acetonitrile, subsequently collected by filtration, and dried, to obtain O-25 (yield amount: 9.26 g, yield ratio: 49%). The structure was identified by $^1$H-NMR (methanol). The results are as follows.

$^1$H-NMR (400 MHz, MeOH-d4): 7.37-7.28 (m, 2H), 7.07-6.98 (m, 3H), 4.61-5.45 (m, 4H), 4.24 (s, 12H), 4.15-4.09 (m, 4H)

Synthesis Example of O-26

In a 100 mL three-neck recovery flask, 7.52 g of 1,4-diazabicyclo[2,2,2]octane (manufactured by FUJIFILM Wako Pure Chemical Corporation), 11.46 g of β-chlorophenetole (manufactured by FUJIFILM Wako Pure Chemical Corporation), and 18.96 g of 2-pyrrolidone were stirred at 70° C. for 16 hours; subsequently, to this, 11.46 g of 2-bromoethanol was added and stirring was performed at 90° C. for 16 hours. The resultant mixture was cooled to room temperature; subsequently, to this, 100 g of water and 50 g of ethyl acetate were added to cause separation, and the aqueous phase was isolated. Subsequently, water in the aqueous phase was driven off under a reduced pressure; to the resultant viscous substance, 40 g of acetonitrile was added and stirring was performed at 60° C. for 1 hour; subsequently, the supernatant component was removed, and subsequently acetonitrile was driven off under a reduced pressure, to obtain O-26 (yield amount: 13.3 g, yield ratio: 51%). The structure was identified by $^1$H-NMR (methanol). The results are as follows.

$^1$H-NMR (400 MHz, MeOH-d4): 7.40-7.29 (m, 2H), 7.14-6.99 (m, 3H), 4.63-4.54 (m, 2H), 4.30 (s, 12H), 4.21-4.15 (m, 2H), 4.14-4.06 (m, 2H), 3.87-3.79 (m, 2H)

Synthesis Example of O-28

In a 300 mL three-neck recovery flask, O-8 (12 g), 8.09 g of benzyl chloride (manufactured by FUJIFILM Wako Pure Chemical Corporation), and 12.0 g of 2-pyrrolidone were stirred at 70° C. for 4 hours; subsequently, to this, 200 g of ethyl acetate was added and subsequently the supernatant component was removed. To the residue, 100 g of acetonitrile was added; the precipitated powder was collected by filtration and dried, to obtain O-28 (yield amount: 16.4 g, yield ratio: 89%). The structure was identified by $^1$H-NMR (methanol). The results are as follows.

$^1$H-NMR (400 MHz, MeOH-d4): 7.66-7.53 (m, 5H), 4.86 (s, 2H), 4.56 (s, 2H), 4.32 (q, J=7.2 Hz, 2H), 4.24 (dd, J=7.5 Hz, 7.4 Hz, 6H), 4.07 (dd, J=7.5 Hz, 7.4 Hz, 6H), 1.30 (t, J=7.2 Hz, 3H)

Preparation of OR-3
As a high-molecular-weight compound OR-3, "PAS-H-1L" manufactured by NITTOBO MEDICAL CO., LTD. was prepared.
Preparation of Oil-Soluble Dyes
Preparation of SB28 and SB3
As oil-soluble dyes, SB28 and SB3 were individually prepared.
SB3 is C.I. Solvent Black 3 (black dye, nonionic azo dye).
SB28 is C.I. Solvent Black 28 (black dye, ionic azo dye).
Synthesis of RB5A
A reactive dye Reactive Black 5 was made to be oil-soluble, to thereby obtain an oil-soluble dye RB5A.
RB5A is a black dye and ionic azo dye.
Hereinafter, it will be described in detail.

inorganic bismuth catalyst; hereafter, also referred to as "U-600") was added, and stirring was performed at 70° C. for 5 hours.
Subsequently, to this, 515.41 g of isopropyl alcohol and 711.75 g of ethyl acetate were added and stirring was performed at 70° C. for 3 hours.
After the 3-hour stirring, the reaction solution was left to cool to room temperature (23° C.), subsequently its concentration was adjusted using ethyl acetate, to thereby obtain a 30 mass % solution of the polymer P (solvent: mixed solution of ethyl acetate/isopropyl alcohol).
Note that a portion of the amount of isopropyl alcohol also functions as a terminal capping agent for the polymer P.

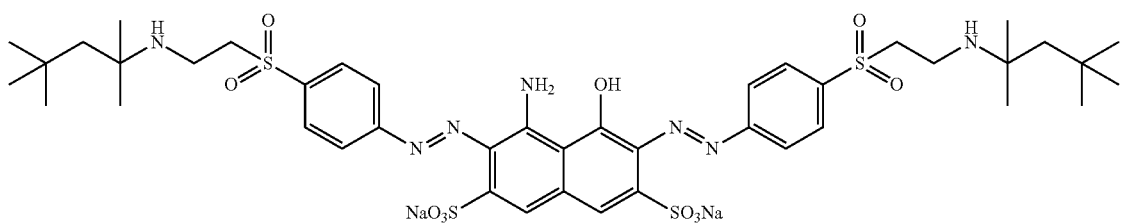

RB5A

Hereinafter, synthesis of the oil-soluble dye RB5A will be described in detail.
In a 300 mL three-neck recovery flask, a solution containing Reactive Black 5 (20 g; manufactured by Aldrich) and 11.84 g of water was stirred at 30° C. for 1 hour; subsequently, to this, 5.1 g of t-octylamine (manufactured by FUJIFILM Wako Pure Chemical Corporation), 31.17 g of ethyl acetate, 10.39 g of methyl ethyl ketone, and 5.71 g of sodium carbonate were added and stirred at 60° C. for 2 hours. Subsequently, to this, 53.4 g of water was added, cooling to 30° C. was performed, and subsequently stirring was performed for 2 hours. The resultant precipitate was collected by filtration and dried, to obtain RB5A. The structure was identified by $^1$H-NMR (DMSO). The results are as follows.
$^1$H-NMR (400 MHz, DMSO-d6): 15.61-15.15 (s, 1H), 10.65-10.48 (d, 2H), 8.29 (d, 2H), 8.18-7.90 (m, 6H), 7.49 (s, 1H), 7.41 (s, 1H), 3.48-3.44 (q, 4H), 2.81-2.72 (q, 4H), 1, 29 (s, 4H), 1.12 (s, 12H), 0.93 (s, 18H)

Example 1

Synthesis of Polymer P
Into a three-neck flask,
as a Unit-(1)-forming compound, 176.2 g of hexamethylene diisocyanate (HDI),
as a hydrophilic-group-introducing compound, 68.1 g of 2,2-dimethylolpropionic acid (DMPA),
as a Unit-(2)-forming compound, 491.9 g of Compound "(2-18) PC T5651" (polycarbonatediol), and
1202.62 g of ethyl acetate
were charged and heated to 70° C.
The Compound "(2-18) PC T5651" is DURANOL (registered trademark) T5651 manufactured by Asahi Kasei Chemicals Corporation (in Table, simply described as "T5651". Mn is 1000. $Rc^1$ and $Rc^2$ are each an alkylene group having 5 or 6 carbon atoms).
Subsequently, into the three-neck flask, 2.454 g of NEOSTANN U-600 (manufactured by Nitto Kasei Co., Ltd., For the polymer P, the types of the compounds (raw materials) for forming the units, Mw, Tg(° C.), and acid value (mmol/g) will be described in Table 1-1.
Preparation of Pretreatment Liquid
The components for providing the following composition were mixed together, to obtain a pretreatment liquid.
Composition of Pretreatment Liquid
  O-1 (specified onium salt compound)
    10 mass %
  2-Pyrrolidone
    16 mass %
  2-Methyl-1,3-propanediol
    9 mass %
  Water
    the remainder of 100 mass % in total
Preparation of Coloring Resin Particle Dispersion
Preparation of Oil-Phase Component
Ethyl acetate, the 30 mass % solution of the polymer P, and the oil-soluble dye (specifically, a black dye that is a chromium complex dye) "SB28" were mixed together and stirred for 15 minutes, to thereby obtain 149.8 g of an oil-phase component having a solid content of 30 mass %.
In the preparation of the oil-phase component, the usage amounts of the 30 mass % solution of the polymer P and SB28 were individually adjusted such that, relative to the solid content of the coloring resin particles to be produced, the polymer P content became 40 mass %,
relative to the solid content of the coloring resin particles to be produced, the SB28 content became 60 mass %, and
in the coloring resin particles to be produced, a mass content ratio [P/dye] (specifically, a ratio of the mass content of the polymer P to the mass content of the oil-soluble dye) became 0.67.
Preparation of Aqueous-Phase Component
Distilled water (135.3 g) and sodium hydroxide serving as a neutralizer were mixed together and stirred for 15 minutes, to thereby prepare an aqueous-phase component.
The usage amount of sodium hydroxide serving as a neutralizer was adjusted such that, in the coloring resin particles to be produced, the degree of neutralization (specifically, the ratio of the number of sodium carboxylate groups to the total number of carboxy groups and sodium carboxylate groups) became 90%.

Preparation of Coloring Resin Particle Dispersion

The oil-phase component and the aqueous-phase component were mixed together, and the resultant mixture was emulsified at room temperature using a homogenizer at 18000 rpm for 10 minutes, to obtain an emulsion. The obtained emulsion was added to 48.0 g of distilled water; the resultant liquid was heated to 50° C. and stirred at 50° C. for 5 hours, to thereby drive off, from the liquid, ethyl acetate and isopropyl alcohol.

The liquid from which ethyl acetate and isopropyl alcohol have been driven off was diluted with distilled water so as to have a solid content amount of 20 mass %, to thereby obtain a black coloring resin particle dispersion containing coloring resin particles and water.

In the coloring resin particle dispersion, the coloring resin particles were found to have a volume-average particle size of 150 nm (the same applied to Examples 2 to 38 and Comparative Examples 1 to 3 described later).

Preparation of Ink

The above-described coloring resin particle dispersion, a surfactant, glycerol, and distilled water described below were mixed together, and the resultant mixture was filtered through a polytetrafluoroethylene (PTFE) membrane filter (pore size: 1 μm), to thereby obtain an ink having the following composition. This ink of Example 1 is a black ink.

Composition of Ink
  Solid content of coloring resin particles (specifically, the solid content in the coloring resin particle dispersion) . . . 10 parts by mass
  Surfactant (manufactured by Nissin Chemical Industry Co., Ltd., "OLFINE E1010") . . . 1 part by mass
  Glycerol . . . 20 parts by mass
  Distilled water . . . 69 parts by mass Ink Jet Textile Printing A combination of the pretreatment liquid and the ink, namely, an ink set was used to perform ink jet textile printing.

The outline is as follows: the pretreatment liquid was used to pretreat a cotton textile; to the pretreated cotton textile, the ink was applied to obtain a colored textile; and the obtained colored textile was heat-treated to thereby obtain a printed textile.

Hereinafter, this will be described in detail.

Pretreatment of Cotton Textile

The pretreatment liquid was caused, by a padding process, to permeate a cotton textile (cotton broad 40, manufactured by SHIKISENSHA CO., LTD.) at a pick up of 60% and drying was performed for 24 hours.

The term "pick up (%)" used herein refers to, in the squeezed textile including the aqueous pretreatment liquid, the residual amount (mass ratio) of the aqueous pretreatment liquid to the textile.

Application of Ink

An ink jet printer (PX-045A, manufactured by SEIKO EPSON CORPORATION) was used to apply the ink to the pretreated cotton textile to form a solid image, to obtain a colored textile. The ink mass per unit area was set at 15 g/m².

Heat Treatment (Heat-Press)

The colored textile was dried at 20° C. for 12 hours.

The dried colored textile was heat-treated using a heat-press machine (desktop automatic flat press machine, model: AF-54TEN, manufactured by Asahi Garment Machinery Co., LTD.) under conditions of 140° C. and 120 seconds. In this way, the solid image in the dried colored textile was heat-treated, to obtain a printed textile.

Evaluations

The ink and the printed textile were subjected to the following evaluations.

The results will be described in Table 1-2.

Optical Density of Printed Textile

The optical density (OD (Optical Density) value) of the printed textile was measured, and evaluation ranks below were used to evaluate the optical density of the printed textile.

The OD value was measured using a colorimeter (Gretag Macbeth Spectrolino, manufactured by X-Rite Inc.).

Of the following evaluation ranks, SSS is the highest rank for the optical density of the printed textile.

Evaluation ranks of optical density of printed textile
  SSS: an OD value of 1.7 or more
  SS: an OD value of 1.6 or more and less than 1.7
  S: an OD value of 1.4 or more and less than 1.6
  A: an OD value of 1.2 or more and less than 1.4
  B: an OD value of 1.0 or more and less than 1.2
  C: an OD value of 0.8 or more and less than 1.0
  D: an OD value of less than 0.8

Washing Resistance of Printed Textile

The washing resistance of the printed textile was evaluated in accordance with ISO 105-006.

Of the evaluation results of the washing resistance of the printed textile, 5 is the highest rank for the washing resistance of the printed textile.

In Table 1-2, in the evaluation results of washing resistance,
  "1-2" means being higher than the rank 1 and lower than the rank 2,
  "2-3" means being higher than the rank 2 and lower than the rank 3,
  "3-4" means being higher than the rank 3 and lower than the rank 4, and
  "4-5" means being higher than the rank 4 and lower than the rank 5.

Texture of Printed Textile

The softness of the printed textile was evaluated, to thereby evaluate the texture of the printed textile. Hereinafter, this will be described in detail.

From the printed textile, an evaluation sample being rectangular and having a length (long side) of 150 mm and a width (short side) of 50 mm was cut out.

As an evaluation jig, a stainless steel plate having a length (long side) of 200 mm, a width (short side) of 100 mm, and a thickness of 1 mm was prepared.

The evaluation jig was placed to stand such that the short-side direction lay in the vertical direction and the long-side direction lay in the horizontal direction.

Subsequently, on a long side of the evaluation jig lying in the horizontal direction, the central portion of the evaluation sample in the longitudinal direction (specifically, the center line) was placed such that both sides of the evaluation sample that were divided in the longitudinal direction (both side edge portions) hung down.

In this state, in the evaluation sample, the distance in a straight line between one of the long-side edge portions and the other long-side edge portion was measured, and evaluation ranks below were used to evaluate the texture of the printed textile. In this evaluation, the softer the evaluation sample (in other words, the better the texture), the lower both sides of the evaluation sample that are divided in the longitudinal direction hang down due to their weights (in other words, the further the evaluation sample bends); this results in, in the evaluation sample, a decrease in the distance in a straight line between one of the long-side edge portions and the other long-side edge portion.

Of the following evaluation ranks, 5 is the highest rank for the texture of the printed textile. The evaluation rank 5 means that the printed textile is extremely soft and easy to bend.

Evaluation Ranks of Texture of Printed Textile
- 5: the distance in the straight line is less than 40 mm.
- 4-5: the distance in the straight line is 40 mm or more and less than 55 mm.
- 4: the distance in the straight line is 55 mm or more and less than 70 mm.
- 3-5: the distance in the straight line is 70 mm or more and less than 85 mm.
- 3: the distance in the straight line is 85 mm or more and less than 100 mm.
- 2: the distance in the straight line is 100 mm or more and less than 115 mm.
- 1: the distance in the straight line is 115 mm or more.

Examples 2 to 28

The same procedures as in Example 1 were performed except that the type of the specified onium salt compound contained in the pretreatment liquid was changed as described in Table 1-1 and Table 2-1.

The results will be described in Table 1-2 and Table 2-2.

Examples 29 to 32

The same procedures were performed as in Example 5 except that the content (mass %) of the specified onium salt compound relative to the total amount of the pretreatment liquid was changed as described in the "Amount (mass %)" column in Table 2-1.

The results will be described in Table 2-2.

Examples 33 to 34

The same procedures were performed as in Example 26 except that the type of the oil-soluble dye contained in the ink was changed as described in Table 2-2.

The results will be described in Table 2-2.

Examples 35 to 38

The same procedures were performed as in Example 6 except for the following points.

The results will be described in Table 2-2.

Points Changed from Example 6

In the synthesis of the polymer P contained in the ink, without changing the total usage mass of the Unit-(1)-forming compound and the Unit-(2)-forming compound or the usage molar ratio [Unit-(2)-forming compound/Unit-(1)-forming compound], the combination of the type of the Unit-(1)-forming compound and the type of the Unit-(2)-forming compound was changed to a combination described in Table 2-1. In Table 2-1, the types of the Unit-(1)-forming compound and the types of the Unit-(2)-forming compound individually correspond to the above-described symbols of the specific examples.

The reaction conditions (reaction temperature and reaction time) were controlled such that the polymer P had a weight-average molecular weight of 15000.

The type of the oil-soluble dye contained in the ink was changed as described in Table 2-2.

Compound "(2-16) PPG" (polypropylene glycol) has a number-average molecular weight (Mn) of 1000.

Compound "(2-22) PEG" (polyethylene glycol) has a number-average molecular weight (Mn) of 1000.

Comparative Examples 1 to 3

The same procedures as in Example 1 were performed except that the specified onium salt compound contained in the pretreatment liquid was changed to a comparative compound described in Table 2-1 and the type of the oil-soluble dye contained in the ink was changed as described in Table 2-2.

The results will be described in Table 2-2.

TABLE 1-1

| | Pretreatment liquid Specified onium salt compound or comparative compound | | | | Ink Coloring resin particles Polymer P or comparative compound | | | | | |
|---|---|---|---|---|---|---|---|---|---|---|
| | | | | | Raw materials | | | Properties of polymer | | |
| | Type | Classification | ClogP | Cation Molecular weight | Amount (mass %) | Hydrophilic-group-introducing compound | Unit-(1)-forming compound | Unit-(2)-forming compound | Mw | Tg (° C.) | Acid value (mmol/g) |
| Example 1 | O-1 | (A1) | −1.72 | 174 | 10 | DMPA | HDI | (2-18) PC T5651 | 15000 | 0 | 0.69 |
| Example 2 | O-2 | (A1) | −2.02 | 180 | 10 | DMPA | HDI | (2-18) PC T5651 | 15000 | 0 | 0.69 |
| Example 3 | O-3 | (A1) | −2.44 | 174 | 10 | DMPA | HDI | (2-18) PC T5651 | 15000 | 0 | 0.69 |
| Example 4 | O-4 | (A1) | −0.66 | 202 | 10 | DMPA | HDI | (2-18) PC T5651 | 15000 | 0 | 0.69 |
| Example 5 | O-5 | (A) | 0.23 | 244 | 10 | DMPA | HDI | (2-18) PC T5651 | 15000 | 0 | 0.69 |
| Example 6 | O-6 | (A) | 1.82 | 287 | 10 | DMPA | HDI | (2-18) PC T5651 | 15000 | 0 | 0.69 |
| Example 7 | O-7 | (A) | −0.04 | 216 | 10 | DMPA | HDI | (2-18) PC T5651 | 15000 | 0 | 0.69 |
| Example 8 | O-8 | (A) | 0.37 | 199 | 10 | DMPA | HDI | (2-18) PC T5651 | 15000 | 0 | 0.69 |
| Example 9 | O-9 | (A2) | −0.01 | 224 | 10 | DMPA | HDI | (2-18) PC T5651 | 15000 | 0 | 0.69 |
| Example 10 | O-10 | (A) | 5.13 | 307 | 10 | DMPA | HDI | (2-18) PC T5651 | 15000 | 0 | 0.69 |
| Example 11 | O-11 | (A1) | −0.96 | 208 | 10 | DMPA | HDI | (2-18) PC T5651 | 15000 | 0 | 0.69 |
| Example 12 | O-12 | (A1) | 1.16 | 264 | 10 | DMPA | HDI | (2-18) PC T5651 | 15000 | 0 | 0.69 |
| Example 13 | O-13 | (A) | 2.32 | 307 | 10 | DMPA | HDI | (2-18) PC T5651 | 15000 | 0 | 0.69 |

TABLE 1-1-continued

| | Pretreatment liquid Specified onium salt compound or comparative compound | | | | Ink Coloring resin particles Polymer P or comparative compound | | | | | | |
|---|---|---|---|---|---|---|---|---|---|---|---|
| | | | | | Raw materials | | | Properties of polymer | | | |
| | Type | Classi-fication | ClogP | Cation Molecular weight | Amount (mass %) | Hydrophilic-group-introducing compound | Unit-(1)-forming compound | Unit-(2)-forming compound | Mw | Tg (° C.) | Acid value (mmol/g) |
| Example 14 | O-14 | (A1) | 0.05 | 220 | 10 | DMPA | HDI | (2-18) PC T5651 | 15000 | 0 | 0.69 |
| Example 15 | O-15 | (A1) | 0.09 | 222 | 10 | DMPA | HDI | (2-18) PC T5651 | 15000 | 0 | 0.69 |
| Example 16 | O-16 | (A1) | 0.34 | 248 | 10 | DMPA | HDI | (2-18) PC T5651 | 15000 | 0 | 0.69 |
| Example 17 | O-17 | (A) | 1.80 | 233 | 10 | DMPA | HDI | (2-18) PC T5651 | 15000 | 0 | 0.69 |
| Example 18 | O-18 | (A1) | 0.19 | 252 | 10 | DMPA | HDI | (2-18) PC T5651 | 15000 | 0 | 0.69 |
| Example 19 | O-19 | (A1) | 0.38 | 300 | 10 | DMPA | HDI | (2-18) PC T5651 | 15000 | 0 | 0.69 |
| Example 20 | O-20 | (B1) | 0.42 | 389 | 10 | DMPA | HDI | (2-18) PC T5651 | 15000 | 0 | 0.69 |
| Example 21 | O-21 | (B1) | 0.10 | 459 | 10 | DMPA | HDI | (2-18) PC T5651 | 15000 | 0 | 0.69 |
| Example 22 | O-22 | (B1) | 1.87 | 595 | 10 | DMPA | HDI | (2-18) PC T5651 | 15000 | 0 | 0.69 |

TABLE 1-2

| | Ink Coloring resin particles Oil-soluble dye | | Evaluation results | | |
|---|---|---|---|---|---|
| | Classification | Type | Optical density | Washing resistance | Texture |
| Example 1 | Ionic | SB28 | S | 4 | 5 |
| Example 2 | Ionic | SB28 | S | 4 | 5 |
| Example 3 | Ionic | SB28 | S | 4 | 5 |
| Example 4 | Ionic | SB28 | S | 4-5 | 5 |
| Example 5 | Ionic | SB28 | S | 4-5 | 5 |
| Example 6 | Ionic | SB28 | S | 4-5 | 5 |
| Example 7 | Ionic | SB28 | S | 4-5 | 5 |
| Example 8 | Ionic | SB28 | S | 4-5 | 5 |
| Example 9 | Ionic | SB28 | S | 4-5 | 5 |
| Example 10 | Ionic | SB28 | S | 4-5 | 5 |
| Example 11 | Ionic | SB28 | SS | 4-5 | 5 |
| Example 12 | Ionic | SB28 | SS | 4-5 | 5 |
| Example 13 | Ionic | SB28 | SS | 4-5 | 5 |
| Example 14 | Ionic | SB28 | SS | 4-5 | 5 |
| Example 15 | Ionic | SB28 | SS | 4-5 | 5 |
| Example 16 | Ionic | SB28 | SS | 4-5 | 5 |
| Example 17 | Ionic | SB28 | SS | 4-5 | 5 |
| Example 18 | Ionic | SB28 | SS | 4-5 | 5 |
| Example 19 | Ionic | SB28 | SS | 4-5 | 5 |
| Example 20 | Ionic | SB28 | SS | 4-5 | 5 |
| Example 21 | Ionic | SB28 | S | 4-5 | 4 |
| Example 22 | Ionic | SB28 | S | 4-5 | 4 |

TABLE 2-1

| | Pretreatment liquid Specified onium salt compound or comparative compound | | | | | Ink Coloring resin particles Polymer P or comparative compound | | | | | |
|---|---|---|---|---|---|---|---|---|---|---|---|
| | | | Cation | | | Hydrophilic- | Unit-(1)- | Unit-(2)- | Raw materials | Properties of polymer | |
| | Type | Classification | ClogP | Molecular weight | Amount (mass %) | group-introducing compound | forming compound | forming compound | Mw | Tg (° C.) | Acid value (mmol/g) |
| Example 23 | O-23 | (B1) | 0.17 | 451 | 10 | DMPA | HDI | (2-18) PC T5651 | 15000 | 0 | 0.69 |
| Example 24 | O-24 | (B2) | 0.27 | 286 | 10 | DMPA | HDI | (2-18) PC T5651 | 15000 | 0 | 0.69 |
| Example 25 | O-25 | (B2) | 3.11 | 355 | 10 | DMPA | HDI | (2-18) PC T5651 | 15000 | 0 | 0.69 |
| Example 26 | O-26 | (B2) | 0.53 | 278 | 10 | DMPA | HDI | (2-18) PC T5651 | 15000 | 0 | 0.69 |
| Example 27 | O-27 | (B2) | 1.69 | 320 | 10 | DMPA | HDI | (2-18) PC T5651 | 15000 | 0 | 0.69 |
| Example 28 | O-28 | (B2) | 0.63 | 290 | 10 | DMPA | HDI | (2-18) PC T5651 | 15000 | 0 | 0.69 |

TABLE 2-1-continued

| | Pretreatment liquid | | | | | Ink Coloring resin particles | | | | | |
|---|---|---|---|---|---|---|---|---|---|---|---|
| | Specified onium salt compound or comparative compound | | | | | Polymer P or comparative compound | | | | | |
| | | | | | | Raw materials | | | Properties of polymer | | |
| | | Cation | | | Hydrophilic- | Unit-(1)- | Unit-(2)- | | | | |
| | Type | Classification | ClogP | Molecular weight | Amount (mass %) | group-introducing compound | forming compound | forming compound | Mw | Tg (° C.) | Acid value (mmol/g) |
| Example 29 | O-5 | (A) | 0.23 | 244 | 5 | DMPA | HDI | (2-18) PC T5651 | 15000 | 0 | 0.69 |
| Example 30 | O-5 | (A) | 0.23 | 244 | 15 | DMPA | HDI | (2-18) PC T5651 | 15000 | 0 | 0.69 |
| Example 31 | O-5 | (A) | 0.23 | 244 | 3 | DMPA | HDI | (2-18) PC T5651 | 15000 | 0 | 0.69 |
| Example 32 | O-5 | (A) | 0.23 | 244 | 23 | DMPA | HDI | (2-18) PC T5651 | 15000 | 0 | 0.69 |
| Example 33 | O-26 | (B2) | 0.53 | 278 | 10 | DMPA | HDI | (2-18) PC T5651 | 15000 | 0 | 0.69 |
| Example 34 | O-26 | (B2) | 0.53 | 278 | 10 | DMPA | HDI | (2-18) PC T5651 | 15000 | 0 | 0.69 |
| Example 35 | O-6 | (A) | 1.82 | 287 | 10 | DMPA | HDI | (2-16) PPG | 15000 | 0 | 0.69 |
| Example 36 | O-6 | (A) | 1.82 | 287 | 10 | DMPA | HDI | (2-22) PEG | 15000 | 0 | 0.69 |
| Example 37 | O-6 | (A) | 1.82 | 287 | 10 | DMPA | XDI | (2-18) PC T5651 | 15000 | 30 | 0.69 |
| Example 38 | O-6 | (A) | 1.82 | 287 | 10 | DMPA | HDI | (2-e) | 15000 | 40 | 0.69 |
| Comparative Example 1 | OR-1 | Comparative | 0.56 | 228 | 10 | DMPA | HDI | T5651 | 15000 | 0 | 0.69 |
| Comparative Example 2 | OR-2 | Comparative | 0.01 | 220 | 10 | DMPA | HDI | T5651 | 15000 | 0 | 0.69 |
| Comparative Example 3 | OR-3 | Comparative | −1.41 | 8500 | 10 | DMPA | HDI | T5651 | 15000 | 0 | 0.69 |

TABLE 2-2

| | Ink Coloring resin particles Oil-soluble dye | | Evaluation results | | |
|---|---|---|---|---|---|
| | Classification | Type | Optical density | Washing resistance | Texture |
| Example 23 | Ionic | SB28 | S | 4-5 | 4 |
| Example 24 | Ionic | SB28 | SS | 4-5 | 5 |
| Example 25 | Ionic | SB28 | SSS | 5 | 5 |
| Example 26 | Ionic | SB28 | SSS | 5 | 5 |
| Example 27 | Ionic | SB28 | SSS | 5 | 5 |
| Example 28 | Ionic | SB28 | SSS | 5 | 5 |
| Example 29 | Ionic | SB28 | S | 4-5 | 5 |
| Example 30 | Ionic | SB28 | S | 4-5 | 5 |
| Example 31 | Ionic | SB28 | S | 4 | 5 |
| Example 32 | Ionic | SB28 | S | 4-5 | 4 |
| Example 33 | Nonionic | SB3 | S | 4 | 5 |
| Example 34 | Ionic | RB5A | SSS | 5 | 5 |
| Example 35 | Ionic | RB5A | S | 4-5 | 5 |
| Example 36 | Ionic | RB5A | S | 4-5 | 5 |
| Example 37 | Ionic | RB5A | S | 4-5 | 5 |
| Example 38 | Ionic | RB5A | S | 4-5 | 5 |
| Comparative Example 1 | Ionic | RB5A | A | 3 | 5 |
| Comparative Example 2 | Ionic | RB5A | S | 3 | 5 |
| Comparative Example 3 | Ionic | RB5A | A | 2 | 2 |

As described in Table 1-1 to Table 2-2, Examples 1 to 38, which each employed a pretreatment liquid containing the specified onium salt compound including at least one of an ether bond, an ester bond, a hydroxy group, or an allyl group, provided printed textiles that had high optical density, high washing resistance, and good texture.

By contrast, Comparative Examples 1 to 3, which each employed a comparative compound not including an ether bond, an ester bond, a hydroxy group, or an allyl group, provided printed textiles that had lowered optical density and lowered washing resistance.

Comparative Example 3, which employed a high-molecular-weight compound as a comparative compound, provided a printed textile that had poor texture (specifically, the printed textile was hard).

The results of Examples 10 and 11 have demonstrated that the case where the specified onium salt compound includes an ammonium cation (Example 11) provides a printed textile that has further improved optical density.

The results of Examples 24 and 25 have demonstrated that the case where the specified onium salt compound includes an aromatic ring (Example 25) provides a printed textile that has further improved optical density and washing resistance.

The results of Examples 20 and 21 have demonstrated that the case where, in the specified onium salt compound, the cation structure has a molecular weight of 400 or less (Example 20) provides a printed textile that has further improved optical density and texture.

Those having been described so far are the Example group employing pretreatment liquids and black inks according to Examples of the present disclosure; however, it is appreciated that cases each employing, instead of such a black ink, or, in addition to the black ink, at least one ink of another color also similarly provide advantages of the pretreatment liquid according to Examples of the present disclosure and, as a result, provide advantages similar to those in the Example group.

The entire contents disclosed by JP2019-180625 filed in the Japan Patent Office on Sep. 30, 2019 are incorporated herein by reference.

All the documents, patent applications, and technical standards mentioned in this Specification are incorporated herein by reference to the same extent as in the case where the documents, patent applications, and technical standards are each specifically and individually described as being incorporated herein by reference.

What is claimed is:

1. A textile printing ink set comprising:
a textile printing pretreatment liquid comprising, water and an onium salt compound represented by Formula (A) below or Formula (B) below,

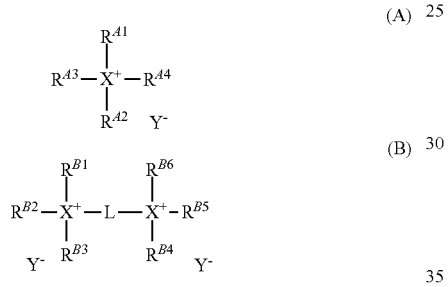

where, in Formula (A),
$R^{A1}$ to $R^{A4}$ each independently represent a hydrocarbon group that may include at least one of an aromatic ring, a hetero ring, an ether bond, an ester bond, or a substituent, at least one of $R^{A1}$ to $R^{A4}$ is a hydrocarbon group that includes at least one of an ether bond,
an ester bond, a hydroxy group, or an allyl group and that may include a substituent,
at least two of $R^{A1}$ to $R^{A4}$ may be bonded together to form a ring,
$X^+$ represents an ammonium cation or a phosphonium cation, and
$Y^-$ represents a counter anion,
in Formula (B),
$R^{B1}$ to $R^{B6}$ each independently represent a hydrocarbon group that may include at least one of a hetero ring, an ether bond, an ester bond, or a substituent,
at least one of $R^{B1}$ to $R^{B6}$ is a hydrocarbon group that includes at least one of an ether bond, an ester bond, a hydroxy group, or an allyl group and that may include a substituent,
at least two of $R^{B1}$ to $R^{B6}$ may be bonded together to form a ring,
two $X^+$'s each independently represent an ammonium cation or a phosphonium cation,
two $Y^-$'s each independently represent a counter anion, and
L represents a divalent linking group; and
a textile printing ink comprising water and coloring resin particles,
wherein the coloring resin particles contain an oil-soluble dye and a polymer P including a hydrophilic group.

2. The textile printing ink set according to claim 1, wherein $X^+$ in Formula (A) and two $X^+$'s in Formula (B) each independently represent an ammonium cation.

3. The textile printing ink set according to claim 1, wherein at least one of $R^{A1}$ to $R^{A4}$ in Formula (A) and at least one of $R^{B1}$ to $R^{B6}$ in Formula (B) are each a hydrocarbon group that includes an aromatic ring and that may include at least one of a hetero ring, an ether bond, an ester bond, or a substituent.

4. The textile printing ink set according to claim 1, wherein, in the onium salt compound represented by Formula (A) or Formula (B), a cation structure has a molecular weight of 400 or less.

5. The textile printing ink set according to claim 1, wherein a content of the onium salt compound represented by Formula (A) or Formula (B) relative to a total amount of the textile printing pretreatment liquid is 5 mass % to 20 mass %.

6. The textile printing ink set according to claim 1, wherein the polymer P further includes a structural unit represented by Formula (1) below and a structural unit represented by Formula (2) below:

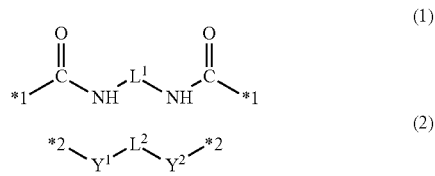

where, in Formula (1),
$L^1$ represents a hydrocarbon group, and
two *1's each represent a bonding site,
in Formula (2),
$L^2$ represents a hydrocarbon group that has 2 to 50 carbon atoms and that may include an oxygen atom, a nitrogen atom, or a sulfur atom, or a polymer chain that is formed of a polyether chain, a polyester chain, a polycaprolactone chain, a polycarbonate chain, a polybutadiene chain, a polyisoprene chain, or a polyolefin chain and that has a number-average molecular weight of 500 or more,
$Y^1$ and $Y^2$ each independently represent —O—, —S—, or —NRz—,
Rz represents a hydrogen atom or a hydrocarbon group having 1 to 20 carbon atoms, and
two *2's each represent a bonding site.

7. The textile printing ink set according to claim 6, wherein $L^2$ in Formula (2) above is a polymer chain that is formed of a polycarbonate chain or a polyether chain and that has a number-average molecular weight of 500 or more.

8. The textile printing ink set according to any one of claim 1, wherein the polymer P has a glass transition temperature of 50° C. or less.

9. The textile printing ink set according to claim 1, wherein the hydrophilic group in the polymer P is at least one selected from the group consisting of a carboxy group and a salt of a carboxy group.

10. The textile printing ink set according to claim 1, wherein the polymer P has a weight-average molecular weight of 8000 to 30000.

11. The textile printing ink set according to claim 1, wherein the oil-soluble dye includes an azo dye having an ionic group.

12. An ink jet textile printing method using the textile printing ink set according to claim 1, the method comprising:
- a step of pretreating a textile by applying the textile printing pretreatment liquid;
- a step of applying the textile printing ink by an ink jet process to the pretreated textile; and
- a step of heat-treating the textile to which the textile printing ink has been applied, to obtain a printed textile.

* * * * *